US011633335B2

United States Patent
Abe et al.

(10) Patent No.: US 11,633,335 B2
(45) Date of Patent: *Apr. 25, 2023

(54) SKIN CLEANSING COMPOSITION

(71) Applicant: KAO CORPORATION, Tokyo (JP)

(72) Inventors: Keita Abe, Koto-ku (JP); Toshiaki Ozawa, Setagaya-ku (JP); Yuri Okutani, Bunkyo-ku (JP); Daisuke Sawa, Chiyoda-ku (JP)

(73) Assignee: KAO CORPORATION, Tokyo (JP)

( * ) Notice: Subject to any disclaimer, the term of this patent is extended or adjusted under 35 U.S.C. 154(b) by 144 days.

This patent is subject to a terminal disclaimer.

(21) Appl. No.: 16/603,953

(22) PCT Filed: Apr. 6, 2018

(86) PCT No.: PCT/JP2018/014723
§ 371 (c)(1),
(2) Date: Oct. 9, 2019

(87) PCT Pub. No.: WO2018/190264
PCT Pub. Date: Oct. 18, 2018

(65) Prior Publication Data
US 2020/0121577 A1 Apr. 23, 2020

(30) Foreign Application Priority Data
Apr. 10, 2017 (JP) .............................. JP2017-077869

(51) Int. Cl.
A61K 8/41 (2006.01)
A61K 8/36 (2006.01)
A61K 8/46 (2006.01)
A61Q 19/10 (2006.01)

(52) U.S. Cl.
CPC ................. *A61K 8/41* (2013.01); *A61K 8/36* (2013.01); *A61K 8/463* (2013.01); *A61K 8/466* (2013.01); *A61Q 19/10* (2013.01)

(58) Field of Classification Search
CPC ............. A61K 8/41; A61K 8/36; A61K 8/463
See application file for complete search history.

(56) References Cited

U.S. PATENT DOCUMENTS

| 5,352,389 A * | 10/1994 | Gazzani ................ A61Q 5/02 510/119 |
| 5,376,310 A * | 12/1994 | Cripe ..................... C11D 1/06 510/108 |
| 6,174,536 B1 | 1/2001 | Crotty et al. |
| 2008/0026974 A1 | 1/2008 | Barnhart et al. |
| 2009/0209443 A1 | 8/2009 | Barnhart et al. |
| 2011/0263471 A1 | 10/2011 | Barnhart et al. |

FOREIGN PATENT DOCUMENTS

| EP | 2 821 053 A1 | 1/2015 | |
| EP | 2 821 054 A1 | 1/2015 | |
| JP | 11-12127 A | 1/1999 | |
| JP | 2001-226241 A | 8/2001 | |
| JP | 2006-206582 A | 8/2006 | |
| JP | 2007-230929 A | 9/2007 | |
| JP | 2008-56912 A | 3/2008 | |
| JP | 2011-12252 A | 1/2011 | |
| JP | 2013-209371 A | 10/2013 | |
| JP | 2015-113307 A | 6/2015 | |
| JP | 2018-177778 A | 11/2018 | |
| JP | 2018-177780 A | 11/2018 | |
| JP | 2018-177781 A | 11/2018 | |
| JP | 2019-89857 A | 6/2019 | |
| WO | WO 2007/145054 A1 | 12/2007 | |
| WO | WO 2013/129652 A1 | 9/2013 | |
| WO | WO 2018/190302 A1 | 10/2018 | |
| WO | WO-2018190301 A1 * | 10/2018 | ........... A61K 31/195 |

OTHER PUBLICATIONS

International Search Report dated May 29, 2018 In PCT/JP2018/014723 filed on Apr. 6, 2018.

Extended European Search Report dated Nov. 13, 2020 in corresponding European Patent Application No. 187841341, 7 pages.

* cited by examiner

Primary Examiner — Necholus Ogden, Jr.
(74) Attorney, Agent, or Firm — Oblon, McClelland, Maier & Neustadt, L.L.P.

(57) ABSTRACT

The present invention relates to a skin cleansing composition which can sufficiently exhibit an excellent keratotic plug-removing effect without a burden such as pain and irritation on the skin. The skin cleansing composition comprises 0.08 mass % or more and 35 mass % or less of (X) 2-amino-2-methyl-1-propanol and has a pH of 9.3 or more and 12.5 or less at 25° C.

17 Claims, No Drawings

SKIN CLEANSING COMPOSITION

FIELD OF THE INVENTION

The present invention relates to a skin cleansing composition comprising 2-amino-2-methyl-1-propanol.

BACKGROUND OF THE INVENTION

Keratotic plugs are observed in the pores at sites with increased sebum secretion, for example, around the nose, and are a substance occluding the pores like in plugs.

If such keratotic plugs are left without being removed, roughness will appear on the skin, and the keratotic plugs physically expand the pores to readily apt to enlarge the openings of the pores. Additionally, the surfaces of the keratotic plugs are also darkened by oxidation, leading to a risk of spoiling the beauty appearance. Furthermore, these cause, for example, acne and readily result in skin troubles, such as rashes and pimples. Based on these facts, keratotic plugs bother many women as one of causes of pore conspicuousness. Accordingly, a variety of techniques for removing such keratotic plugs have been conventionally developed.

For example, Patent Literature 1 discloses a skin cleansing composition containing an organic acid, such as lactic acid, and an N-acyl taurine anionic surfactant and having a pH of 3 to 5, the composition being capable of exhibiting a keratotic plug-removing effect while providing good foaming and so on. Patent Literature 2 discloses a cleansing agent composition containing a specific nonionic surfactant, an oil having a viscosity of 15 mPa·s or less at 30° C., a water-soluble polymer and so on. Patent Literature 3 discloses a facial cleanser containing a dibasic acid diester having 6 to 20 carbon atoms. In all of these, the function of removing keratotic plugs is achieved by specific oils.

In contrast, Patent Literature 4 discloses a sheet pack composed of a multi-layer moisture-permeable support and a cosmetic containing a polymer compound having a salt-forming group, such as a carboxyl group. Such a sheet pack is applied onto the skin to impart a smooth feeling, a moisture feeling, etc. to the skin and also can exhibit a keratotic plug-removing effect when peeled from the skin.
(Patent Literature 1) JP-A-2015-113307
(Patent Literature 2) JP-A-2011-12252
(Patent Literature 3) JP-A-2007-230929
(Patent Literature 4) JP-A-11-12127

SUMMARY OF THE INVENTION

The present invention relates to a skin cleansing composition which can sufficiently exhibit an excellent keratotic plug-removing effect without a burden, such as pain and irritation, on the skin.

That is, the present invention provides a skin cleansing composition comprising 0.08 mass % or more and 35 mass % or less of (X) 2-amino-2-methyl-1-propanol and having a pH of 9.3 or more and 12.5 or less at 25° C.

The present invention also provides a skin cleansing composition comprising 0.08 mass % or more and 35 mass % or less of (X) 2-amino-2-methyl-1-propanol and also (Z) one or two selected from the group consisting of 2-amino-2-hydroxymethyl-1,3-propanediol and 2-amino-2-methyl-1,3-propanediol and having a pH of 8.3 or more and 12.5 or less at 25° C.

In the skin cleansing composition described in Patent Literature 1, only the liquid sebum, desquamation, and keratotic plugs partially protruding from the pores on the skin are removed mainly by the detergency of the anionic surfactant. In the cleansing compositions described in Patent Literatures 2 and 3, since the effect of removing keratotic plugs is produced by mainly the solubility of, for example, a specific oil, only a part of keratotic plugs in a state of being easily removed is removed. That is, any of the techniques described in these patent literatures does not directly remove the dirt in the pores, and improvement is still necessary for sufficiently removing keratotic plugs.

In contrast, the sheet pack physically exhibiting the effect of physically removing keratotic plugs described in Patent Literature 4 can directly remove keratotic plugs and can achieve a significant reduction in pore clogging. However, in recent years, such a physical removal means causes anxiety of hurting the skin, and a technique of removing keratotic plugs with reduced pain and irritation on the skin is desired.

Accordingly, the present inventors diligently studied to solve the above-mentioned problems and, as a result, found that a skin cleansing composition which can more effectively remove keratotic plugs without causing, for example, excessive pain or irritation on the skin can be obtained by controlling the pH within a specific range while using a specific amount of 2-amino-2-methyl-1-propanol.

According to the skin cleansing composition of the present invention, keratotic plugs can be effectively removed without placing a burden on the skin, and pore clogging and pore opening can be significantly suppressed to effectively avoid pore conspicuousness. In addition, it is possible to feel that the skin after removal of keratotic plugs is fine, soft, and bright and beautiful without darkening.

DETAILED DESCRIPTION OF THE INVENTION

The present invention will now be described in detail.

In the present specification, the term "keratotic plug" refers to a substance physiologically formed in pores of human skin and occluding the pores like a plug. The main components of the keratotic plug are a horny layer and proteins derived from a hair follicle. The keratotic plug is formed of a material in which these main components are mixed with proteins including proteins derived from acne bacteria or *Staphylococcus aureus* and proteins derived from cellular organelles such as lysosomes and lipids including triglyceride, free fatty acids, and lipid peroxides.

The skin cleansing composition of the present invention contains 0.08 mass % or more and 35 mass % or less of 2-amino-2-methyl-1-propanol as component (X) and has a pH of 9.3 or more and 12.5 or less at 25° C. Thus, by containing a specific amount of 2-amino-2-hydroxymethyl-1,3-propanediol as component (X) in a skin cleansing composition and controlling a pH within a specific range, the composition containing component (X) quickly penetrates into keratotic plugs and can effectively elute lipids and the like forming the keratotic plugs. In general, proteins, such as the horny layer, readily aggregate and are hardly removed with a cleanser or the like. However, the composition containing component (X) applied to the skin can suppress protein aggregation in parallel and can therefore effectively remove keratotic plugs, although the keratotic plugs contain proteins. Furthermore, when the applied composition is washed away with water, water can readily penetrate into the keratotic plugs. Consequently, the keratotic plugs are further broken down by the penetration of water and can be thoroughly washed away, resulting in effective removal of keratotic plugs containing proteins and lipids from pores. In addition, the composition can soften the skin around the pores after the removal of keratotic plugs and make the skin moisty, fine, soft, bright, and beautiful, while exhibiting the excellent keratotic plug-removing effect.

The above-mentioned component, 2-amino-2-methyl-1-propanol (X2) is specifically represented by the following formula (x2) and is also simply called "AMP".

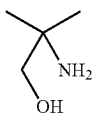

(x2)

Such component has a molecular weight of 89.14, a melting point of 30° C. to 31° C., and a boiling point of 165.5° C. (10 mmHg). Component (X2) has a pKa of 9.72 at 25° C. and is readily dissolved in water.

The content of component (X) in the skin cleansing composition of the present invention is 0.08 mass % or more, preferably 0.1 mass % or more, more preferably 0.5 mass % or more, further preferably 0.8 mass % or more, further preferably 1 mass % or more, further preferably 2 mass % or more, further preferably 3 mass % or more, further preferably 4 mass % or more, and further preferably 5 mass % or more from the viewpoint of a good combination of a keratotic plug-removing effect and a protein aggregation-suppressing effect. In addition, the content of component (X) in the skin cleansing composition of the present invention is 35 mass % or less, preferably 30 mass % or less, more preferably 25 mass % or less, further preferably 20 mass % or less, further preferably 15 mass % or less, further preferably 12 mass % or less, further preferably 11 mass % or less, and further preferably 10 mass % or less from the viewpoint of preventing an increase in irritation to the skin. The content of component (X) in the skin cleansing composition of the present invention is preferably from 0.08 to 35 mass %, more preferably from 0.1 to 30 mass %, further preferably from 0.5 to 25 mass %, further preferably from 0.8 to 20 mass %, further preferably from 1 to 15 mass %, further preferably from 2 to 12 mass %, further preferably from 3 to 11 mass %, further preferably from 4 to 10 mass %, and further preferably from 5 to 10 mass %.

Component (X) mentioned above is preferably present in a free form, instead of a salt form, in the skin cleansing composition from the viewpoint of improving the detergency against keratotic plug. That is, preferably, component (X) does not form a salt, such as a fatty acid salt, together with an acidic component, such as an unneutralized fatty acid and is at least partially present in a free form so that component (X) is independently present in the skin cleansing composition. The mass ratio of the content of component (X) present in a free form to the content of component (X), (content of free-form component (X))/(content of component (X)), is preferably 0.6 or more, more preferably 0.8 or more, further preferably 0.9 or more, and further preferably 1.0, from the viewpoint mentioned above.

The pH of the skin cleansing composition of the present invention at 25° C. is 9.3 or more, preferably 9.5 or more, more preferably 9.8 or more, further preferably 10.0 or more, further preferably 10.2 or more and further preferably 10.5 or more from the viewpoint of sufficiently exhibiting the keratotic plug-removing effect of component (X). In addition, the pH of the skin cleansing composition of the present invention at 25° C. is 12.5 or less, preferably 12.2 or less, further preferably 12.0 or less, further preferably 11.8 or less and further preferably 11.5 or less from the viewpoint of preventing an excessive burden on the skin. In addition, the pH of the skin cleansing composition of the present invention at 25° C. is from 9.3 to 12.5, preferably from 9.5 to 12.2, more preferably from 9.8 to 12.0, further preferably from 10.0 to 11.8, further preferably from 10.2 to 11.5 and further preferably from 10.5 to 11.5

Such a pH is a level suitable for sufficiently exhibiting a desired effect, especially, even when the skin cleansing composition of the present invention does not contain component (Z) described below.

The skin cleansing composition of the present invention may appropriately contain a pH conditioner, such as sodium hydroxide, sodium carbonate, sodium citrate, or hydrochloric acid, to adjust the pH within the above-mentioned range.

The skin cleansing composition of the present invention may further contain (A) an anionic surfactant, in addition to the above-mentioned components, from the viewpoint of improving the foaming property. Preferably, from the viewpoint of further enhancing the keratotic plug-removing effect, the composition further contains (A1) an anionic surfactant having a carboxylic acid group and/or (A2) an anionic surfactant having a sulfonic acid group or a sulfate group as the anionic surfactant (A).

The term "carboxylic acid group" of the anionic surfactant having a carboxylic acid group as component (A1) includes a carboxylate residue. The anionic surfactant having a carboxylic acid group as component (A1) include one or more selected from the group consisting of a fatty acid or a salt thereof, an ether carboxylic acid or a salt thereof, and an N-acylamino acid salt, and include more preferably an ether carboxylic acid or a salt thereof.

The fatty acid or salt thereof that can be used as component (A1) is, from the viewpoint of exhibiting good foaming property and further enhancing the keratotic plug-removing effect, preferably a fatty acid or a salt thereof having a linear or branched alkyl group having 10 to 22 carbon atoms, more preferably a fatty acid or a salt thereof having a linear or branched alkyl group having 10 to 18 carbon atoms, and further preferably a fatty acid or a salt thereof having a linear alkyl group having 12 to 14 carbon atoms.

Specifically, examples thereof include one or more selected from the group consisting of lauric acid, myristic acid, palmitic acid, stearic acid, behenic acid, and a salt thereof. In particular, from the same viewpoint as above, component (A1) includes preferably one or more selected from the group consisting of a laurate, a myristate, and a palmitate; and more preferably one or two selected from the group consisting of a laurate and a myristate.

The salt constituting the fatty acid salt as component (A1) includes preferably one or more selected from the group consisting of an alkali metal and ammonium, more preferably one or more selected from the group consisting of an alkali metal, and further preferably a sodium salt.

The skin cleansing composition may contain, as component (A1), for example, a fatty acid salt formed from an unneutralized fatty acid and a neutralizer. The neutralization rate of the fatty acid is preferably from 50% to 100%, more preferably from 70% to 100%, further preferably from 90% to 100%, and further preferably 100%, from the viewpoint of improving the volume of foam and foaming property. The neutralizer is specifically preferably one or two selected from the group consisting of potassium hydroxide and sodium hydroxide.

Examples of the ether carboxylic acid or salt thereof that can be used as component (A1) include an ether carboxylic acid or a salt thereof represented by the following Formula (1):

$$R^1O(CH_2CH_2O)_mCH_2COOM^1 \quad (1)$$

wherein $R^1$ represents an alkyl or alkenyl group having 10 to 22 carbon atoms; m represents a number of 0.5 to 10 on average; and $M^1$ represents a hydrogen atom, an alkali metal, an alkaline earth metal, ammonium, or organic ammonium.

In Formula (1), $R^1$ is preferably an alkyl group having 12 to 16 carbon atoms and more preferably an alkyl group having 12 to 14 carbon atoms from the viewpoint of exhibiting a good foaming property and further enhancing the keratotic plug-removing effect. From the same viewpoint as above, the average addition mole number m of ethylene oxide is preferably from 2 to 5.

Examples of $M^1$ includes a hydrogen atom; an alkali metal such as sodium or potassium; an alkaline earth metal such as calcium or magnesium; ammonium; alkanolamine-derived ammonium such as monoethanolamine, diethanolamine, or triethanolamine; or basic amino acid-derived ammonium such as arginine or lysine. Among them, from the same viewpoint as above, $M^1$ preferably represents one or more selected from the group consisting of sodium, potassium, triethanolamine, and arginine; and more preferably one or two selected from the group consisting of sodium and potassium.

From the same viewpoint as above, specifically, the ether carboxylic acid or salt thereof includes preferably one or more selected from the group consisting of polyoxyethylene lauryl ether carboxylate, polyoxyethylene myristyl ether carboxylate, and polyoxyethylene palmityl ether carboxylate; more preferably one or two selected from the group consisting of polyoxyethylene lauryl ether carboxylate and polyoxyethylene myristyl ether carboxylate; and further preferably polyoxyethylene lauryl ether carboxylate.

Commercially available examples of the ether carboxylic acid or salt thereof include AKYPO RLM 45CA (manufactured by Kao Corporation) and AKYPO LM 26C (manufactured by Kao Corporation).

The composition may contain, as component (A1), for example, an ether carboxylate formed from an unneutralized ether carboxylic acid and a neutralizer. The neutralization rate of the ether carboxylic acid is preferably form 50% to 100%, more preferably from 70% to 100%, further preferably from 90% to 100%, and further preferably 100% from the viewpoint of improving the volume of foam and foaming property. The neutralizer is specifically preferably one or two selected from the group consisting of potassium hydroxide and sodium hydroxide.

Examples of the acylamino acid salt that can be used as component (A1) include an N-acylamino acid or salt thereof. The acyl group of the N-acylamino acid or salt thereof is preferably derived from a saturated or unsaturated, linear or branched fatty acid having 4 to 30 carbon atoms, more preferably derived from a saturated or unsaturated, linear or branched fatty acid having 6 to 26 carbon atoms, and further preferably derived from a saturated or unsaturated, linear or branched fatty acid having 8 to 24 carbon atoms, from the viewpoint of exhibiting a good foaming property and further enhancing the keratotic plug-removing effect. Examples of such a fatty acid include caprylic acid, capric acid, lauric acid, myristic acid, palmitic acid, stearic acid, and oleic acid. Among these fatty acids, from the same viewpoint as above, one or more selected from the group consisting of lauric acid, myristic acid, palmitic acid, and oleic acid are preferable; and lauric acid is more preferable. The acyl group of the N-acylamino acid may be derived from a mixture of the above-mentioned fatty acids, for example, one obtained from coconut oil, palm kernel oil, or the like, as ae raw material. In particular, one obtained preferably from a coconut oil fatty acid and palm kernel fatty acid as a raw material is preferable; and one obtained from a coconut oil fatty acid as a raw material is more preferable.

The amino acid portion of the N-acylamino acid or salt thereof is preferably a neutral amino acid selected from the group consisting of glycine and alanine or an acidic amino acid selected from the group consisting of glutamic acid and aspartic acid, more preferably an acidic amino acid, and further preferably glutamic acid, from the viewpoint of exhibiting a good foaming property and further enhancing the keratotic plug-removing effect. The amino acid portion may be the D-form, the L-form, or a mixture of D- and L-forms and is preferably the L-form.

The N-acylamino acid or salt thereof may be used singly or in combinations of two or more thereof. In particular, from the viewpoint of a good foaming property and improving the smoothness of the skin, the N-acylamino acid or salt thereof includes preferably at least one selected from the group consisting of N-lauroyl glutamic acid, N-myristoyl glutamic acid, N-cocoyl glutamic acid, N-palm fatty acid glutamic acid, N-lauroyl aspartic acid, N-cocoyl glycine, N-cocoyl alanine, and a salt thereof; more preferably at least one selected from the group consisting of N-lauroyl glutamic acid, N-myristoyl glutamic acid, N-cocoyl glutamic acid, N-palm fatty acid glutamic acid, N-lauroyl aspartic acid, N-cocoyl glycine, and a salt thereof; further preferably at least one selected from the group consisting of N-lauroyl glutamic acid, N-myristoyl glutamic acid, N-cocoyl glutamic acid, N-lauroyl aspartic acid, and a salt thereof; further preferably at least one selected from the group consisting of N-cocoyl glutamic acid, N-lauroyl aspartic acid, and a salt thereof; and further preferably N-cocoyl glutamic acid or a salt thereof.

The salt of the N-acylamino acid or salt thereof is preferably at least one salt selected from the group consisting of an alkali metal salt, a triethanolamine salt, and an arginine salt; more preferably at least one salt selected from the group consisting of a sodium salt, a potassium salt, and a triethanolamine salt; further preferably at least one salt selected from the group consisting of a sodium salt and a potassium salt; and further preferably a sodium salt, from the viewpoint of reducing irritation to the skin and easiness of acquisition.

The N-acylamino acid to be used is prepared by neutralization with a base. The neutralization rate of the N-acylamino acid preferably from 80% to 100%, more preferably from 90% to 100%, and further preferably 100% from the viewpoint of improving the volume of foam and foaming property. The neutralizer is specifically preferably one or more selected from the group consisting of potassium hydroxide and sodium hydroxide.

The content of component (A1) in the skin cleansing composition of the present invention is preferably 0.01 mass % or more, more preferably 0.05 mass % or more, further preferably 0.10 mass % or more, and further preferably 0.3 mass % or more; and preferably 5 mass % or less, more preferably 3 mass % or less, further preferably 2.0 mass % or less, further preferably 1.5 mass % or less, and further preferably 1.0 mass % or less from the viewpoint of exhibiting a good foaming property. The content of component (A1) in the skin cleansing composition of the present invention is preferably from 0.01 to 5 mass %, more preferably from 0.05 to 3 mass %, further preferably from 0.05 to 2.0 mass %, further preferably from 0.10 to 1.5 mass %, and further preferably from 0.3 to 1.0 mass %.

The "content" of component (A1) refers to the amount in terms of a fatty acid when the fatty acid or salt thereof mentioned above is used as component (A) and refers to the amount in terms of an acid when the ether carboxylic acid or salt thereof or the N-acylamino acid or salt thereof is used.

In the skin cleansing composition of the present invention, the mass ratio of the content of component (X) to the content of component (A1), (X)/(A1), is preferably 0.1 or more, more preferably 0.5 or more, further preferably 1.0 or more, further preferably 2 or more, further preferably 5 or more, and further preferably 8 or more from the viewpoint of exhibiting an excellent keratotic plug-removing effect. In addition, the mass ratio of the content of component (X) to the content of component (A1), (X)/(A1), is preferably 100 or less, more preferably 80 or less, further preferably 70 or less, further preferably 60 or less, further preferably 50 or less, further preferably 40 or less, further preferably 30 or less, and further preferably 20 or less from the viewpoint of exhibiting an excellent keratotic plug-removing effect and maintaining a good foaming property. The mass ratio of the content of component (X) to the content of component (A1), (X)/(A1), is preferably from 0.1 to 100, more preferably from 0.5 to 80, further preferably from 1.0 to 70, further preferably from 2 to 60, further preferably from 2 to 50, further preferably from 5 to 40, further preferably from 8 to 30, and further preferably from 8 to 20.

The term "sulfonic acid group or sulfate group" of the anionic surfactant having a sulfonic acid group or sulfate group as component (A2) means including a sulfonate residue or sulfate residue. Examples of such an anionic surfactant having a sulfonic acid group or sulfate group as component (A2) include one or more selected from the group consisting of an alkylbenzene sulfonic acid or a salt thereof, an alkanesulfonic acid or a salt thereof, an alkenylsulfonic acid or a salt thereof, an alkylsulfonic acid or a salt thereof, an acylisethionic acid or a salt thereof, an alkyl sulfate or a salt thereof, an alkyl ether sulfate or a salt thereof, an alkyl sulfosuccinic acid or a salt thereof, a sulfofatty acid methyl ester or a salt thereof, a fatty acid alkanolamide sulfate or a salt thereof, and a monoacylglycerol sulfate or a salt thereof. The salt constituting component (A2) is preferably an inorganic salt selected from the group consisting of a sodium salt, a potassium salt, a lithium salt, a magnesium salt, and an ammonium salt; or an organic amine salt selected from the group consisting of a monoethanolamine salt, a diethanolamine salt, and a triethanolamine salt.

Among them, from the viewpoint of maintaining a good foaming property while exhibiting an excellent keratotic plug-removing effect, component (A2) includes preferably one or more selected from the group consisting of an alkylbenzene sulfonic acid or a salt thereof, an acylisethionic acid or a salt thereof, an alkyl sulfate or a salt thereof, an alkyl ether sulfate or a salt thereof, an alkenylsulfonic acid or a salt thereof, and an alkylsulfonic acid or a salt thereof; more preferably one or more selected from the group consisting of an alkyl sulfate or a salt thereof, an alkyl ether sulfate or a salt thereof, an alkenylsulfonic acid or a salt thereof, and an alkylsulfonic acid a salt thereof; further preferably one or more selected from the group consisting of an alkyl sulfate salt, an alkyl ether sulfate salt, an alkenylsulfonic acid salt, and an alkylsulfonic acid salt.

Examples of the alkyl sulfate salt that can be used as component (A2) include an alkyl sulfate salt represented by the following Formula (2):

$$R^2OSO_3M^2 \qquad (2)$$

wherein $R^2$ represents an aliphatic hydrocarbon group having 8 to 22 carbon atoms; and $M^2$ represents a cation selected from the group consisting of an alkali metal, an alkaline earth metal, ammonium, alkyl ammonium, alkanol ammonium, and glucammonium.

In Formula (2), $R^2$ preferably represents an aliphatic hydrocarbon group having 8 to 18 carbon atoms, more preferably an aliphatic hydrocarbon group having 8 to 16 carbon atoms, and further preferably an aliphatic hydrocarbon group having 10 to 16 carbon atoms from the viewpoint of maintaining a good foaming property while exhibiting an excellent keratotic plug-removing effect. Furthermore, $R^2$ preferably represents an alkyl or alkenyl group having 8 to 16 carbon atoms, more preferably an alkyl or alkenyl group having 10 to 16 carbon atoms, and further preferably an alkyl or alkenyl group having 10 to 14 carbon atoms.

$M^2$ preferably represents, from the same viewpoint as above, an alkali metal or ammonium, more preferably an alkali metal, and further preferably a sodium salt.

Specifically, examples of the alkyl sulfate salt include sodium lauryl sulfate, triethanolamine lauryl sulfate, ammonium lauryl sulfate, sodium myristyl sulfate, sodium cetyl sulfate, sodium stearyl sulfate, sodium oleyl sulfate, and triethanolamine oleyl sulfate. Among them, the alkyl sulfate salt preferably includes one or more selected from the group consisting of sodium lauryl sulfate, triethanolamine lauryl sulfate, and ammonium lauryl sulfate. These compounds may be used singly or in combinations of two or more thereof.

Commercially available examples of the alkyl sulfate salt include EMAL 0S (manufactured by Kao Corporation, sodium lauryl sulfate), EMAL 10PT (manufactured by Kao Corporation, sodium lauryl sulfate), EMAL TD (manufactured by Kao Corporation, triethanolamine lauryl sulfate), and EMAL AD-25R (manufactured by Kao Corporation, ammonium lauryl sulfate).

Examples of the alkyl ether sulfate salt that can be used as component (A2) include an alkyl ether sulfate salt represented by the following Formula (3):

$$R^3O(CH_2CH_2O)_nSO_3M^3 \qquad (3)$$

wherein $R^3$ represents an aliphatic hydrocarbon group having 8 to 22 carbon atoms; $M^3$ represents a cation selected from the group consisting of an alkali metal, alkaline earth metal, ammonium, alkyl ammonium, alkanol ammonium, and glucammonium; and n represents an average addition mole number and is from 0.5 to 20.

In Formula (3), $R^3$ preferably represents an aliphatic hydrocarbon group having 8 to 18 carbon atoms, more preferably an aliphatic hydrocarbon group having 8 to 16 carbon atoms, and further preferably an aliphatic hydrocarbon group having 10 to 16 carbon atoms from the viewpoint of maintaining a good foaming property while exhibiting an excellent keratotic plug-removing effect. Furthermore, $R^3$ preferably represents an alkyl or alkenyl group having 8 to 16 carbon atoms, more preferably an alkyl or alkenyl group having 10 to 16 carbon atoms, and more further preferably an alkyl or alkenyl group having 10 to 14 carbon atoms.

n represents preferably 0.5 or more and preferably 12 or less, more preferably 5 or less, further preferably 4 or less, and further preferably 2 or less, from the same viewpoint as above. Specifically, the range of n is preferably from 0.5 to 12, more preferably from 0.5 to 5, further preferably from 0.5 to 4, and further preferably from 0.5 to 2.

$M^3$ preferably represents an alkali metal or ammonium, more preferably an alkali metal, and further preferably a sodium salt, from the same viewpoint as above.

Specifically, examples of the alkyl ether sulfate salt include one or more selected from the group consisting of sodium polyoxyethylene (1) lauryl ether sulfate, ammonium polyoxyethylene (1) lauryl ether sulfate, sodium polyoxyethylene (1) myristyl ether sulfate, sodium polyoxyethylene (2) lauryl ether sulfate, and sodium polyoxyethylene (2) myristyl ether sulfate. Among them, the alkyl ether sulfate salt preferably includes one or more selected from the group consisting of sodium polyoxyethylene (1) lauryl ether sulfate, ammonium polyoxyethylene (1) lauryl ether sulfate, and sodium polyoxyethylene (2) lauryl ether sulfate. In the present specification, the numbers in parentheses shown in these compounds each mean the average addition mole number of ethylene oxide.

Commercially available examples of the alkyl ether sulfate salt include EMAL 125HP (manufactured by Kao Corporation, sodium polyoxyethylene (1) lauryl ether sulfate), EMAL 125A (manufactured by Kao Corporation, ammonium polyoxyethylene (1) lauryl ether sulfate), and EMAL 227 (manufactured by Kao Corporation, sodium polyoxyethylene (2) lauryl ether sulfate).

The alkenylsulfonic acid or salt thereof that can be used as component (A2) is preferably an alkenylsulfonic acid or salt thereof which is a linear hydrocarbon having 12 to 22 carbon atoms and a double bond, and more preferably a linear hydrocarbon having 12 to 18 carbon atoms and a double bond, and having a sulfo group bound to a carbon atom other than the terminal carbon atoms. The alkenylsulfonic acid or salt thereof is further preferably an alkenylsulfonic acid or salt thereof which is a linear hydrocarbon having 12 to 18 carbon atoms and a double bond, in which the double bond is present at 3- or higher internal position of the linear hydrocarbon in 70 mass % or more thereof and which has a sulfo group bound to a carbon atom other than the terminal carbon atoms.

These alkenylsulfonic acid having 12 to 22 carbon atoms or salts thereof may be used singly or in combinations of two or more thereof and are preferably used in combination of two or more thereof according to the purpose of use from the viewpoint of the foaming property and being capable of controlling the foam quality. Furthermore, an alkenylsulfonic acid having 16 carbon atoms or a salt thereof and an alkenylsulfonic acid having 18 carbon atoms or a salt thereof are preferable from the viewpoint of the foaming property and foam quality. In addition, the alkenylsulfonic acid having 16 carbon atoms or a salt thereof and the alkenylsulfonic acid having 18 carbon atoms or a salt thereof are preferably used as a mixture. In such a case, the mass ratio of the alkenylsulfonic acid having 16 carbon atoms or salt thereof to the alkenylsulfonic acid having 18 carbon atoms or salt thereof is preferably from 1/9 to 9/1, more preferably from 2/8 to 8/2, and further preferably from 5/5 to 2/8. The use of the mixture can enhance the feeling during rinsing.

Examples of the salt constituting the alkenylsulfonic acid salt include an alkali metal such as sodium and potassium; an alkaline earth metal such as calcium and magnesium; ammonium; and a salt constituted of organic ammonium derived from monoethanolamine, diethanolamine, triethanolamine, or the like. Among them, an alkali metal salt and ammonium salt are preferable from the viewpoint of market availability.

The alkylsulfonic acid or salt thereof that can be used as component (A2) is preferably a hydroxyalkylsulfonic acid having 12 to 22 carbon atoms or a salt thereof, more preferably a hydroxyalkylsulfonic acid having 12 to 22 carbon atoms or a salt thereof and having a sulfo group bound to any of the carbon atoms other than the terminal carbon atoms, and further preferably a hydroxyalkylsulfonic acid having 12 to 18 carbon atoms or a salt thereof and having a sulfo group bound to a carbon atom other than the terminal carbon atoms. Further preferably, the hydroxyalkylsulfonic acid or salt thereof is preferably a hydroxyalkylsulfonic acid or salt which is a linear hydrocarbon having 12 to 18 carbon atoms and having a hydroxyl group bound to any of the carbon atoms other than the terminal carbon atoms and a sulfo group bound to any of the carbon atoms other than the terminal carbon atoms.

The hydroxyalkylsulfonic acid having 12 to 22 carbon atoms or salt thereof may be used singly or in combinations of two or more thereof and are preferably used in combination of two or more thereof according to the purpose of use from the viewpoint of the foaming property and being capable of controlling the foam quality. Furthermore, a hydroxyalkylsulfonic acid having 16 carbon atoms or a salt thereof and a hydroxyalkylsulfonic acid having 18 carbon atoms or a salt thereof are preferable from the viewpoint of the foaming property and foam quality. In addition, the hydroxyalkylsulfonic acid having 16 carbon atoms or salt thereof and the hydroxyalkylsulfonic acid having 18 carbon atoms or salt thereof are preferably used as a mixture. In such a case, the mass ratio of the hydroxyalkylsulfonic acid having 16 carbon atoms or salt thereof to the hydroxyalkylsulfonic acid having 18 carbon atoms or salt thereof, (hydroxyalkylsulfonic acid having 16 carbon atoms or salt thereof/hydroxyalkylsulfonic acid having 18 carbon atoms or salt thereof), is preferably from 9/1 to 1/9, more preferably from 8/2 to 2/8, and further preferably from 5/5 to 2/8. The use of the mixture can enhance the feeling during rinsing.

Examples of the salt constituting the alkylsulfonic acid salt include an alkali metal such as sodium and potassium; an alkaline earth metal such as calcium and magnesium; ammonium; and a salt constituted of organic ammonium derived from monoethanolamine, diethanolamine, triethanolamine, or the like. Among them, an alkali metal salt and ammonium salt are preferable from the viewpoint of market availability.

Component (A2) may be an alkenylsulfonic acid or a salt thereof or an alkylsulfonic acid or a salt thereof or may be a mixture of an alkenylsulfonic acid or a salt thereof and an alkylsulfonic acid or a salt thereof. In the mixture, the mass ratio of the alkenylsulfonic acid or salt thereof to the alkylsulfonic acid or salt thereof, (alkenylsulfonic acid or salt thereof/alkylsulfonic acid or salt thereof), is preferably from 5/95 to 50/50 and more preferably from 10/90 to 30/70.

The alkenylsulfonic acid or salt thereof and the alkylsulfonic acid or salt thereof can be produced by, for example, the method described in JP-A-2015-28123.

The content of component (A2) in the skin cleansing composition of the present invention is preferably 0.01 mass % or more, more preferably 0.03 mass % or more, further preferably 0.05 mass % or more, further preferably 0.10 mass % or more, further preferably 0.2 mass % or more, further preferably 0.3 mass % or more, and further preferably 0.5 mass % or more from the viewpoint of exhibiting a good keratotic plug-removing effect and foaming property. The content of component (A2) in the skin cleansing composition of the present invention is preferably 20 mass % or less, more preferably 18 mass % or less, further preferably 15 mass % or less, further preferably 12 mass % or less, further preferably 10 mass % or less, further preferably 8 mass % or less, further preferably 5 mass % or less, further preferably 4 mass % or less, and further preferably 3 mass % or less from the viewpoint of exhibiting a good keratotic plug-removing effect and foaming property. The content of component (A2) in the skin cleansing composition of the present invention is preferably from 0.01 to 20 mass %, more preferably from 0.03 to 18 mass %, further preferably from 0.05 to 18 mass %, further preferably from 0.10 to 15 mass %, further preferably from 0.2 to 12 mass %, further preferably from 0.2 to 10 mass %, from 0.2 to 8 mass %, further preferably from 0.3 to 5 mass %, further preferably from 0.3 to 4 mass %, and further preferably from 0.5 to 3 mass %.

In the skin cleansing composition of the present invention, the mass ratio of the content of component (X) to the content of component (A2), (X)/(A2), is preferably 0.005 or more, more preferably 0.01 or more, further preferably 0.10 or more, further preferably 0.20 or more, further preferably 0.25 or more, further preferably 0.3 or more, and further preferably 0.5 or more from the viewpoint of maintaining a good foaming property. The mass ratio of the content of component (X) to the content of component (A2), (X)/(A2), is preferably 100 or less, more preferably 60 or less, further preferably 50 or less, further preferably 40 or less, further preferably 30 or less, further preferably 20 or less, further preferably 15 or less, further preferably 14 or less, and further preferably 12.5 or less from the viewpoint of preventing an increase in the burden on the skin and exhibiting an excellent keratotic plug-removing effect. The mass ratio of the content of component (X) to the content of component (A2), (X)/(A2), is preferably from 0.005 to 100, more preferably from 0.01 to 60, further preferably from 0.10 to 50, further preferably from 0.20 to 40, further preferably from 0.20 to 30, further preferably from 0.20 to 20, further preferably from 0.25 to 15, further preferably from 0.3 to 14, and further preferably from 0.5 to 12.5.

The skin cleansing composition of the present invention may contain an anionic surfactant other than components (A1) and (A2). Examples of the anionic surfactant other than components (A1) and (A2) include a phosphate surfactant, and specific examples thereof include an alkyl phosphate, a polyoxyethylene alkyl ether phosphate, an alkylaryl ether phosphate, and a fatty acid amide ether phosphoric acid.

Although the content of the anionic surfactant other than components (A1) and (A2) varies depending on the dosage form of the skin cleansing composition of the present invention, the content in the composition is preferably 0.01 mass % or more, more preferably 0.05 mass % or more, and further preferably 0.1 mass % or more; and preferably 10 mass % or less, more preferably 5 mass % or less, further preferably 1.0 mass % or less, and further preferably 0.5 mass % or less from the viewpoint of maintaining a good foaming property while exhibiting an excellent keratotic plug-removing effect. The content of the anionic surfactant other than components (A1) and (A2) in the skin cleansing composition of the present invention is preferably from 0.01 to 10 mass %, more preferably from 0.05 to 5 mass %, further preferably from 0.1 to 1.0 mass %, and further preferably from 0.1 to 0.5 mass %.

The total content of component (A) in the skin cleansing composition of the present invention is preferably 0.01 mass % or more, more preferably 0.02 mass % or more, further preferably 0.05 mass % or more, further preferably 0.1 mass % or more, further preferably 0.3 mass % or more, and further preferably 0.5 mass % or more from the viewpoint of exhibiting good foaming property. The content of component (A) in the skin cleansing composition of the present invention is preferably 30 mass % or less, more preferably 20 mass % or less, further preferably 15 mass % or less, further preferably 12 mass % or less, further preferably 8 mass % or less, and further preferably 4 mass % or less from the viewpoint of preventing an increase in the burden on the skin. The content of component (A) in the skin cleansing composition of the present invention is preferably from 0.01 to 30 mass %, more preferably from 0.02 to 20 mass %, further preferably from 0.05 to 15 mass %, further preferably from 0.1 to 12 mass %, further preferably from 0.3 to 8 mass %, and further preferably from 0.5 to 4 mass %.

The skin cleansing composition of the present invention preferably further contains (B) a nonionic surfactant from the viewpoint of exhibiting good sebum cleansing ability and makeup removability and further enhancing the keratotic plug-removing effect.

Component (B) preferably includes (B1) a nonionic surfactant having an HLB of 11 or more from the viewpoint of enhancing the sebum cleansing ability and the keratotic plug-removing effect. The HLB of such component (B1) is 11 or more, preferably 12 or more and more preferably 13 or more; and preferably 20 or less, more preferably 19 or less, and further preferably 18 or less. Component (B1) has an HLB of 11 or more, preferably from 11 to 20, more preferably from 12 to 19, and further preferably from 13 to 18.

Herein, the HLB (Hydrophilic-Lypophilic Balance) of a nonionic surfactant indicates the molecular weight of the hydrophilic group moiety accounting for the total molecular weight of the surfactant, and is determined by the following equation of Griffin:

$HLB=20\times$(molecular weight of hydrophilic group moiety in surfactant molecule/molecular weight of surfactant).

Examples of the nonionic surfactant as component (B1) include a polyglycerol fatty acid ester, a polyethylene glycol fatty acid ester, a polyoxyethylene glycerol fatty acid ester, a polyoxyethylene polyoxypropylene glycol, a polyoxyethylene sorbitan fatty acid ester, a polyoxyethylene sorbitol fatty acid ester, a polyoxyethylene castor oil, a polyoxyethylene hydrogenated castor oil, a polyoxyethylene hydrogenated castor oil fatty acid ester, a polyoxyethylene alkyl ether, a polyoxyethylene alkyl ether fatty acid ester, a sucrose fatty acid ester, an alkyl polyglucoside, and a (poly)alkyl glyceryl ether.

In particular, from the viewpoint of improving sebum cleansing ability and rinsing performance, component (B1) includes preferably one or more selected from the group consisting of a polyglycerol fatty acid ester, a polyethylene glycol fatty acid ester, a polyoxyethylene glycerol fatty acid ester, a polyoxyethylene sorbitan fatty acid ester, a polyoxyethylene hydrogenated castor oil fatty acid ester, a polyoxyethylene alkyl ether, and an alkyl polyglucoside, and more preferably one or more selected from the group consisting of a polyethylene glycol fatty acid ester, a polyoxyethylene alkyl ether, a polyoxyethylene sorbitan fatty acid ester, and an alkyl polyglycoside.

The commercial product of the polyoxyethylene sorbitan fatty acid ester is preferably, for example, polyoxyethylene (6) sorbitan monolaurate (RHEODOL TW-L106 (HLB: 13.3), manufactured by Kao Corporation).

The commercial product of the polyethylene glycol fatty acid ester is preferably, for example, polyethylene glycol monolaurate (12EO) (EMANON 112 (HLB: 13.7), manufactured by Kao Corporation).

The commercial product of the polyoxyethylene alkyl ether is preferably, for example, polyoxyethylene (21) lauryl ether (EMLGEN 121-G (HLB: 16.6), manufactured by Kao Corporation), polyoxyethylene (20) 2-hexyldecyl ether (EMULGEN 1620G (HLB: 14), manufactured by Kao Corporation), polyoxyethylene (16) lauryl ether (EMULGEN 116 (HLB: 15.8), manufactured by Kao Corporation), polyoxyethylene (9) lauryl ether (EMULGEN 109P (HLB: 13.6), manufactured by Kao Corporation), polyoxyethylene (20) octyldodecyl ether (EMULGENT 2020G (HLB: 13.3), manufactured by Kao Corporation), or polyoxyethylene (25) octyldodecyl ether (EMULGEN 2025G (HLB: 14.1), manufactured by Kao Corporation).

The commercial product of the alkyl polyglucoside is preferably, for example, dodecyl glucoside (MYDOL 10 (HLB: 15.7), manufactured by Kao Corporation) or lauryl glucoside (MYDOL 12 (HLB: 17), manufactured by Kao Corporation).

Component (B) preferably contains (B2) a nonionic surfactant having an HLB of less than 11 from the viewpoint of exhibiting better makeup removability. The HLB of component (B2) is less than 11, preferably 10 or less and more preferably 9 or less; and preferably 4 or more, more preferably HLB 5 or more, and further preferably HLB 6 or more. The HLB of component (B2) is less than 11, preferably from 4 to 10, more preferably from 5 to 10, and further preferably from 6 to 9.

Examples of the nonionic surfactant as component (B2) include a polyethylene glycol surfactant, i.e., an ethylene glycol fatty acid ester such as ethylene glycol monostearate, a polyethylene glycol fatty acid ester such as polyethylene glycol (2) monostearate, a polyethylene glycol alkyl ether such as polyethylene glycol (5) decyl pentadecyl ether, and a polyethylene glycol hydrogenated castor oil such as polyethylene glycol (5) hydrogenated castor oil monoisolaurate; a propylene glycol surfactant, i.e., a propylene glycol fatty acid ester, a polypropylene glycol fatty acid ester, a propylene glycol alkyl ether, a polypropylene glycol alkyl ether, and an ethylene oxide derivative of propylene glycol alkyl ether; a glycerol fatty acid ester such as glycerol monoisostearate; a glycerol alkyl ether such as glycerol monoisostearyl ether; a sorbitan fatty acid ester such as sorbitan monostearate; and a polyglycerol fatty acid ester such as polyglyceryl monoisostearate.

In particular, component (B2) preferably includes one or more selected from the group consisting of a polyoxyethylene alkyl ether and a polyglycerol fatty acid ester.

The commercial product of the polyoxyethylene alkyl ether is preferably, for example, polyoxyethylene (2) lauryl ether (EMULGEN 102 (HLB: 6.4), manufactured by Kao Corporation), polyoxyethylene (3) lauryl ether (EMULGEN 103 (HLB: 8.3), manufactured by Kao Corporation), or polyoxyethylene (5) lauryl ether (EMULGEN 105 (HLB: 10), manufactured by Kao Corporation).

The commercial product of the polyglycerol fatty acid ester is preferably, for example, polyglyceryl isostearate (Cosmol 41V (HLB: 8), manufactured by The Nisshin OilliO Group, Ltd.).

In the skin cleansing composition of the present invention, the mass ratio of the content of the nonionic surfactant having an HLB of 11 or more as component (B1) to the content of the nonionic surfactant having an HLB of less than 11 as component (B2), (B1)/(B2), is preferably 0.1 or more, more preferably 0.6 or more, further preferably 0.8 or more, further preferably 1.5 or more, further preferably 2.5 or more, and further preferably 5 or more; and preferably 25 or less, more preferably 20 or less, further preferably 16 or less, further preferably 14 or less, and further preferably 12 or less from the viewpoint of exhibiting good sebum cleansing ability and makeup removability. The mass ratio of the content of the nonionic surfactant having an HLB of 11 or more as component (B1) and the content of the nonionic surfactant having an HLB of less than 11 as component (B2), (B1)/(B2), is preferably from 0.1 to 25, more preferably from 0.6 to 20, further preferably from 0.8 to 16, further preferably from 1.5 to 14, further preferably from 2.5 to 12, and further preferably from 5 to 12.

The content of component (B) in the skin cleansing composition of the present invention is preferably 0.1 mass % or more, more preferably 0.4 mass % or more, and further preferably 0.5 mass % or more; and preferably 30 mass % or less, more preferably 25 mass % or less, further preferably 20 mass % or less, further preferably 15 mass % or less, and further preferably 10 mass % or less from the viewpoint of exhibiting good sebum cleansing ability and makeup removability and further enhancing the keratotic plug-removing effect. The content of component (B) in the skin cleansing composition of the present invention is preferably from 0.1 to 30 mass %, more preferably from 0.4 to 25 mass %, further preferably from 0.5 to 20 mass %, further preferably from 0.5 to 15 mass %, and further preferably from 0.5 to 10 mass %.

In the skin cleansing composition of the present invention, the mass ratio of the content of component (X) to the content of component (B), (X)/(B), is preferably 0.01 or more, more preferably 0.02 or more, further preferably 0.03 or more, further preferably 0.1 or more, further preferably 0.3 or more, and further preferably 0.5 or more from the viewpoint of exhibiting an excellent keratotic plug-removing effect and improving the sebum cleansing ability and the makeup removability. In the skin cleansing composition of the present invention, the mass ratio of the content of component (X) to the content of component (B), (X)/(B), is preferably 50 or less, more preferably 30 or less, further preferably 25 or less, further preferably 20 or less, and further preferably 15 or less from the viewpoint of exhibiting an excellent keratotic plug-removing effect. In the skin cleansing composition of the present invention, the mass ratio of the content of component (X) to the content of component (B), (X)/(B), is preferably from 0.01 to 50, more preferably from 0.02 to 30, further preferably from 0.03 to 25, further preferably from 0.1 to 25, further preferably from 0.3 to 20, further preferably from 0.5 to 20, and further preferably from 0.5 to 15.

The skin cleansing composition of the present invention can further contain (C) an ampholytic surfactant from the viewpoint of improving the foaming property. Examples of the ampholytic surfactant include an amide amino acid surfactant, a carbobetaine surfactant, an amidobetaine surfactant, an amidosulfobetaine surfactant, and a sulfobetaine surfactant.

Although the content of the ampholytic surfactant varies depending on the dosage form of the skin cleansing composition of the present invention, the content in the skin cleansing composition of the present invention is preferably 0.1 mass % or more, more preferably 0.5 mass % or more, and further preferably 1 mass % or more; and preferably 15 mass % or less, more preferably 10 mass % or less, and further preferably 5 mass % or less from the viewpoint of enhancing the keratotic plug-removing effect and imparting an excellent foaming property. The content of component (C) in the skin cleansing composition of the present invention is preferably from 0.1 to 15 mass %, more preferably from 0.5 to 10 mass %, and further preferably from 1 to 5 mass %.

The skin cleansing composition of the present invention preferably further contains (D) a polyol from the viewpoint of imparting moist feeling to the skin while exhibiting an excellent keratotic plug-removing effect. Examples of the polyol as component (D) include a divalent alcohol such as ethylene glycol, diethylene glycol, polyethylene glycol, propylene glycol, dipropylene glycol, polypropylene glycol, isoprene glycol, hexylene glycol, and 1,3-butylene glycol; a tri- or higher valent alcohol such as glycerol, diglycerol, triglycerol, tetraglycerol, hexaglycerol, decaglycerol, and trimethyl propanol; and a sugar and a sugar alcohol such as erythritol, pentaerythritol, dipentaerythritol, glucose, mannose, galactose, sucrose, fructose, maltose, trehalose, multitol, xylitol, inositol, sorbitan, and sorbitol. In particular, from the viewpoint of imparting moist feeling to the skin and exhibiting an excellent keratotic plug-removing effect, component (D) includes preferably one or more selected from the group consisting of ethylene glycol, diethylene glycol, polyethylene glycol, propylene glycol, dipropylene glycol, polypropylene glycol, isoprene glycol, hexylene glycol, 1,3-butylene glycol, glycerol, diglycerol, triglycerol, tetraglycerol, hexaglycerol, decaglycerol, trimethyl propanol, erythritol, pentaerythritol, dipentaerythritol, glucose, mannose, galactose, sucrose, fructose, maltose, maltitol, xylitol, inositol, sorbitan, and sorbitol; and preferably one or more selected from the group consisting of dipropylene glycol, 1,3-butylene glycol, glycerol, sorbitol, and mannitol.

The content of component (D) in the skin cleansing composition of the present invention is preferably 0.5 mass % or more, more preferably 1 mass % or more, further preferably 3 mass % or more, further preferably 5 mass % or more, further preferably 8 mass % or more, and 10 mass % or more; and preferably 40 mass % or less, more preferably 35 mass % or less, further preferably 30 mass % or less, further preferably 25 mass % or less, and further preferably 20 mass % or less from the viewpoint of exhibiting an excellent keratotic plug-removing effect and imparting moist feeling to the skin. The content of component (D) in the skin cleansing composition of the present invention is preferably from 0.5 to 40 mass %, more preferably from 1 to 35 mass %, further preferably from 3 to 30 mass %, further preferably from 5 to 25 mass %, further preferably from 8 to 20 mass %, and further preferably from 10 to 20 mass %.

The skin cleansing composition of the present invention preferably further contains (E) a water-soluble polymer from the viewpoint of suppressing dropping during application and improving stability over time while exhibiting an excellent keratotic plug-removing effect. The water-soluble polymer as component (E) may be any polymer that is generally used in known skin cleansing compositions. Specifically, suitable examples of the water-soluble polymer include a carboxyvinyl polymer, an acrylic acid/alkyl (meth)acrylate copolymer, and cellulose to which a hydroxyethyl group or a hydroxypropyl group has been added, from the viewpoint of suppressing dropping during application and improving stability over time. The commercial products that can be used as the carboxyvinyl polymer are, for example, Carbopol 981 and Carbopol 981 (manufactured by Lubrizol Advanced Materials, Inc.), and those as the acrylic acid/alkyl (meth)acrylate copolymer are, for example, Carbopol 980 and Carbopol 981 (manufactured by Lubrizol Advanced Materials, Inc.). The commercial products that can be used as the acrylic acid/alkyl (meth)acrylate copolymer are, for example, Pemulen TR-1, Pemulen TR-2, Carbopol ETD2020, Carbopol 1382, Carbopol 1342, Carbopol Ultrez 10, Carbopol Ultrez 20, and Carbopol Ultrez 21 (manufactured by Lubrizol Advanced Materials, Inc.) and AQUPEC HV-501ER (manufactured by Sumitomo Seika Chemicals Co., Ltd.).

In the cellulose to which a hydroxyethyl group or a hydroxypropyl group has been added, hydrogen atoms in the hydroxyl groups of the cellulose are partially substituted with hydroxyethyl groups or hydroxypropyl groups, and the cellulose may have a substituent other than these substituents. Specifically, examples of such cellulose include hydroxyethyl cellulose, hydroxypropyl cellulose, hydroxyethyl methyl cellulose, and hydroxypropyl methyl cellulose. Such cellulose is prepared by reacting cellulose with sodium hydroxide to prepare alkali cellulose and subsequently applying, for example, methyl chloride, monochloroacetic acid, ethylene oxide, or propylene oxide to the alkali cellulose to substitute hydrogen atoms of the hydroxy groups in the cellulose with a hydroxyethyl group, hydroxypropyl group, methyl group, carboxymethyl group, etc.

The average degree of substitution of the cellulose is higher than 0 and preferably 0.5 or more; and more preferably 3 or less and more preferably 2 or less from the viewpoint of suppressing dropping during application and improving stability over time. The weight average molecular weight is, from the same viewpoint as above, preferably 200,000 or more, more preferably 500,000 or more, and more preferably 650,000 or more; and preferably 3,000,000 or less, more preferably 2,000,000 or less, and further preferably 1,600,000 or less. In the present invention, the average degree of substitution is determined by NMR, and the weight average molecular weight is measured with a gel permeation chromatography (GPC)-multiangle laser light scattering (MALLS) detection system using polyethylene oxide as a standard substance.

The cellulose to which a hydroxyethyl group or a hydroxypropyl group has been added is preferably hydroxyethyl cellulose or hydroxypropyl methyl cellulose having preferably an average degree of substitution of 0.5 to 2 and a weight average molecular weight of 650,000 to 1,600,000.

The cellulose to which a hydroxyethyl group or a hydroxypropyl group has been added can be a commercial product such as CELLOSIZE QP52000H (manufactured by The Dow Chemical Company) or HEC Daicel SE400, SE500, SE600, SE850, or SE900 (manufactured by Daicel FineChem Ltd.), as the hydroxyethyl cellulose; or METOLOSE 60SH or 65SH (manufactured by Shin-Etsu Chemical Co., Ltd.) or BENECEL E50, E4M, E10M, F4MC, K99C, K4M, K15M, K35M, K100M, or K200M (manufactured by ASHLAND Inc.) as the hydroxypropyl methyl cellulose.

The content of component (E) in the skin cleansing composition of the present invention is preferably 0.01 mass % or more, more preferably 0.05 mass % or more, further preferably 0.10 mass % or more, and further preferably 0.15 mass % or more; and preferably 3 mass % or less, more preferably 2 mass % or less, further preferably 1 mass % or less, and further preferably 0.8 mass % or less from the viewpoint of exhibiting an excellent keratotic plug-removing effect, suppressing dropping during application, and improving stability over time. The content of component (E) in the skin cleansing composition of the present invention is preferably from 0.01 to 3 mass %, more preferably from 0.05 to 2 mass %, further preferably from 0.10 to 1 mass %, and further preferably from 0.15 to 0.8 mass %.

The skin cleansing composition of the present invention preferably further contains (F) one or more selected from the group consisting of a neutral amino acid, a betaine compound, and an ethylenediamine tetraacetate from the viewpoint of imparting moist feeling to the skin while exhibiting an excellent keratotic plug-removing effect. Examples of the neutral amino acid as component (F) include glycine, sarcosine, L-serine, β-alanine, and aminobutyric acid. Examples of the betaine compound other than component (C) include trimethyl glycine, trimethyl serine, hydroxyethyl dimethyl glycine, and monoethanol-C5-carboxybetaine. In particular, from the viewpoint of exhibiting an excellent keratotic plug-removing effect, component (F) includes preferably one or more selected from the group consisting of trimethyl glycine, trimethyl serine, hydroxyethyl dimethyl glycine, and monoethanol-C5-carboxybetaine; more preferably one or more selected from the group consisting of trimethyl glycine, trimethyl serine, and hydroxyethyl dimethyl glycine; and further preferably trimethyl glycine.

The content of component (F) in the skin cleansing composition of the present invention is preferably 0.1 mass % or more, more preferably 0.5 mass % or more, and further preferably 1.0 mass % or more; and preferably 20 mass % or less, more preferably 15 mass % or less, and further preferably 10 mass % or less from the viewpoint of imparting moist feeling to the skin while exhibiting an excellent keratotic plug-removing effect. The content of component (F) in the skin cleansing composition of the present invention is preferably from 0.1 to 20 mass %, more preferably from 0.5 to 15 mass %, and further preferably from 1.0 to 10 mass %.

The skin cleansing composition of the present invention contains (G) water from the viewpoint of satisfactorily dissolving or dispersing the components mentioned above and the viewpoint of imparting good feeling after washing to the skin applied with the composition. The content of water in the skin cleansing composition of the present invention is preferably 10 mass % or more, more preferably 20 mass % or more, and further preferably 30 mass % or more; and preferably 99.9 mass % or less, more preferably 99.5 mass % or less, and further preferably 99 mass % or less.

Preferably, the skin cleansing composition of the present invention further contains (Z) one or two selected from the group consisting of (X1) 2-amino-2-hydroxymethyl-1,3-propanediol and (X3) 2-amino-2-methyl-1,3-propanediol from the viewpoint of improving the softness of the skin and further enhancing the keratotic plug-removing effect.

The above-mentioned component, 2-amino-2-hydroxymethyl-1,3-propanediol, is specifically represented by the following formula (x1) and is also called "tris(hydroxymethyl)aminomethane" or "Tris".

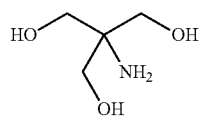
(x1)

Such component has a molecular weight of 121.14, a melting point of 169° C. to 173° C., and a boiling point of 219° C. to 220° C. (10 mmHg). The component (X1) has a pKa of 8.03 at 25° C. indicating weak-basic properties and is readily dissolved in water.

The above-mentioned component, 2-amino-2-methyl-1,3-propanediol, is specifically represented by the following formula (x3) and is also simply called "AMPD".

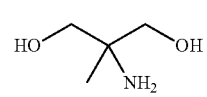
(x3)

Such component has a molecular weight of 105.14, a melting point of 107° C. to 112° C., and a boiling point of 151° C. (10 mmHg). The component (X3) has a pKa of 8.76 at 25° C. and is readily dissolved in water.

In particular, from the viewpoint of the keratotic plug-removing effect, it is preferable to contain both 2-amino-2-hydroxymethyl-1,3-propanediol (X1) and 2-amino-2-methyl-1,3-propanediol (X3).

The content of component (Z) in the skin cleansing composition of the present invention is preferably 0.1 mass % or more, more preferably 0.5 mass % or more, further preferably 0.8 mass % or more, and further preferably 1 mass % or more from the viewpoint of a good combination of a keratotic plug-removing effect and a protein aggregation-suppressing effect. In addition, the content of component (Z) in the skin cleansing composition of the present invention is preferably 15 mass % or less, more preferably 12 mass % or less, further preferably 11 mass % or less, and further preferably 10 mass % or less from the viewpoint of preventing an increase in irritation to the skin. The content of component (Z) in the skin cleansing composition of the present invention is preferably from 0.1 to 15 mass %, more preferably from 0.5 to 12 mass %, further preferably from 0.8 to 11 mass %, and further preferably from 1 to 10 mass %.

Component (Z) is preferably present in a free form, instead of a salt form, in the composition from the viewpoint of improving the detergency against keratotic plugs. That is, preferably, component (Z) does not form a salt, such as a fatty acid salt, together with an acidic component, such as an unneutralized fatty acid and is at least partially present in a free form so that component (Z) is independently present in the composition. The mass ratio of the content of component (Z) present in a free form to the content of component (Z), (content of free-form component (Z))/(content of component (Z)), is preferably 0.6 or more, more preferably 0.8 or more, further preferably 0.9 or more, and further preferably 1.0 from the viewpoint mentioned above.

In the skin cleansing composition of the present invention, the mass ratio of the content of component (X) to the content of component (Z), (X)/(Z), is preferably 0.001 or more, more preferably 0.05 or more, further preferably 0.08 or more, and further preferably 0.1 or more from the viewpoint of enhancing the keratotic plug-removing effect while suppressing the burden on the skin. In addition, the mass ratio of the content of component (X) to the content of component (Z), (X)/(Z), is preferably 100 or less, more preferably 50 or less, further preferably 20 or less, and further preferably 10 or less from the viewpoint of sufficiently exhibiting the skin-softening effect while suppressing the burden on the skin. The mass ratio of the content of component (X) to the content of component (Z), (X)/(Z), is preferably from 0.001 to 100, more preferably from 0.05 to 50, further preferably from 0.08 to 20, and further preferably from 0.1 to 10.

In the skin cleansing composition of the present invention, the total content of component (X) and component (Z) in the skin cleansing composition of the present invention is preferably 0.08 mass % or more, more preferably 0.1 mass % or more, further preferably 0.5 mass % or more, further preferably 0.8 mass % or more, further preferably 1 mass % or more, further preferably 2 mass % or more, further preferably 3 mass % or more, further preferably 4 mass % or more, further preferably 5 mass % or more, and further preferably higher than 5 mass % from the viewpoint of a good combination of a keratotic plug-removing effect and a protein aggregation-suppressing effect. In addition, the total content of component (X) and component (Z) in the skin cleansing composition of the present invention is preferably 35 mass % or less, more preferably 30 mass % or less, further preferably 25 mass % or less, further preferably 20 mass % or less, further preferably 15 mass % or less, further preferably 12 mass % or less, further preferably 11 mass % or less, and further preferably 10 mass % or less from the viewpoint of preventing an increase in irritation to the skin. The total content of component (X) and component (Z) in the skin cleansing composition of the present invention is preferably from 0.08 to 35 mass %, more preferably from 0.1 to 30 mass %, further preferably from 0.5 to 25 mass %, further preferably from 0.8 to 20 mass %, further preferably from 1 to 15 mass %, further preferably from 2 to 12 mass %, further preferably from 3 to 11 mass %, further preferably from 4 to 10 mass %, and further preferably from 5 to 10 mass %, and further preferably higher than 5 mass % and 12 mass % or less.

The case of using a skin cleansing composition containing component (X) and component (Z) tends to broaden the pH range capable of showing excellent keratotic plug-removing effect, compared to the case of a composition not containing component (Z). The pH of the skin cleansing composition of the present invention containing component (X) and component (Z) at 25° C. is preferably 8.3 or more, more preferably 8.5 or more, further preferably 8.8 or more, further preferably 9.0 or more, further preferably 9.2 or more, further preferably 9.3 or more, further preferably 9.5 or more, further preferably 9.8 or more, and further preferably 10.0 or more from the viewpoint of sufficiently exhibiting the keratotic plug-removing effect by component (X) together with component (Z). In addition, the pH of the skin cleansing composition of the present invention containing component (X) and component (Z) at 25° C. is preferably 12.5 or less, more preferably 12.2 or less, further preferably 12.0 or less, further preferably 11.8 or less, further preferably 11.5 or less, further preferably 11.2 or less, and further preferably 11.0 or less from the viewpoint of preventing an excessive burden on the skin. The pH of the skin cleansing composition of the present invention containing component (X) and component (Z) at 25° C. is preferably from 8.3 to 12.5, more preferably from 8.5 to 12.2, further preferably from 8.8 to 12.0, further preferably from 8.8 to 11.8, further preferably from 9.0 to 11.5, further preferably from 9.2 to 11.2, further preferably from 9.3 to 11.2, further preferably from 9.5 to 11.0, further preferably from 9.8 to 11.0, and further preferably from 10.0 to 11.0.

The skin cleansing composition of the present invention containing component (X) and component (Z) may appropriately contain a pH conditioner, such as sodium hydroxide, sodium carbonate, sodium citrate, or hydrochloric acid.

The skin cleansing composition of the present invention can contain components that are generally used in known skin cleansing compositions, in addition to the above-described components, within a range not impairing the effects of the present invention. Examples of such components include an oil such as a hydrocarbon oil, an ester oil, an ether oil, and a vegetable oil; a moisturizing agent other than components (D) and (E) such as sodium lactate, urea, and sodium pyrrolidone carboxylate; an ultraviolet absorber; an antioxidant; a disinfectant; an extract; a perfume; and a dye.

Each of these agents is not limited to its usual use, and may be used as other applications according to the purpose. For example, an antiperspirant may be used for other uses, such as using as a perfume. Alternatively, for example, an antiperspirant may be used for more than one use, such as using an agent having effects as an antiperspirant and a perfume.

The skin cleansing composition of the present invention can be used as, for example, a cosmetic, a quasi-drug, or a medicine without any particular limitation. In particular, from the viewpoint of sufficiently benefiting from the excellent keratotic plug-removing effect, the composition can be used as a keratotic plug-removing skin cleansing composition, can be suitably used as a pore-cleansing skin cosmetic for suppressing pore conspicuousness, and in particular, can be suitably used as a keratotic plug-removing skin cosmetic.

The dosage form of the skin cleansing composition of the present invention is not particularly limited and is preferably a foam, liquid, paste, cream, or some other dosage form, more preferably a foam or liquid dosage form from the viewpoint of improving the penetration into keratotic plugs. The skin cleansing composition of the present invention can be used as facial cleanser, makeup cleansing cosmetic, body cleanser, scalp cleanser, pack, or massage cosmetic. In particular, the composition is preferably used as, for example, facial cleanser, makeup cleansing cosmetic, body cleanser, or scalp cleanser.

The site to which the skin cleansing composition of the present invention is applied is preferably the skin of a body, more preferably the skin of, for example, face, neck, limbs, or torso, excluding the scalp, further preferably the pore sites on such skin area, and further preferably the pore sites on the skin from forehead to nose tip.

The use form of the skin cleansing composition of the present invention can be as follows: the skin cleansing composition is applied to the above-mentioned application site and, after a certain period of time, the composition remaining on the application site is washed away with water or is wiped away with a wiping material such as tissue, nonwoven fabric, or woven fabric, preferably washed away with water. The application means can be appropriately selected depending on the application site and so on. For example, when the dosage form of the skin cleansing composition of the present invention is a liquid, paste, cream, or some other dosage form, the skin cleansing composition may be directly applied to the application site. Specifically, the skin cleansing composition is applied to an application site in an amount of preferably from 0.05 to 2 mL/cm$^2$, more preferably from 0.1 to 1 mL/cm$^2$; the application site is then massaged for usually from 10 seconds to 10 minutes, preferably from 15 seconds to 5 minutes, more preferably from 30 seconds to 4 minutes, and further preferably from 1 to 3 minutes; and the composition remaining on the application site is subsequently washed away with water or wiped away with a wiping material such as tissue, nonwoven fabric, or woven fabric and is desirably washed away with water.

For example, when the dosage form of the skin cleansing composition of the present invention is a liquid dosage form, the composition can also be used as a sheet-form cleansing agent by impregnating a sheet material such as unwoven fabric or woven fabric with the composition. Specifically, a sheet-form cleansing agent impregnated with the skin cleansing composition is attached onto an application site and is left to stand for usually from 1 to 30 minutes, preferably from 5 to 20 minutes, and further preferably from 10 to 15 minutes, and the sheet-form cleansing agent is then peeled off. The composition remaining on the application site is then washed away with water or wiped away with a wiping material such as tissue, nonwoven fabric, or woven fabric, and is desirably washed away with water.

Furthermore, when the skin cleansing composition of the present invention is in a foam dosage form, for example, a foam discharge container is filled with the skin cleansing composition in the liquid form, and the composition may be discharged from the container onto the application site in use. After the discharging, the same procedure as that in the use form of the application may be carried out. Such a foam dosage form is suitable for massaging the application site.

A spray container or high-pressure washer is filled with the skin cleansing composition of the present invention, and the composition may be sprayed from the nozzle in use. In such a case, the composition is sprayed onto the application site for usually from 10 seconds to 5 minutes, preferably from 15 seconds to 3 minutes, and further preferably from 30 seconds to 2 minutes to wash the application site. Subsequently, the composition remaining on the application site is then washed away with water or wiped away with a wiping material, such as tissue, nonwoven fabric, or woven fabric, and is desirably washed away with water.

The skin cleansing composition of the present invention can be prepared by, for example, a production process including step (I) of heating water to 60° C. to 80° C. in advance, step (II) of sequentially adding component (X) and other components as needed to the water obtained in step (I) and mixing and stirring, and step (III) of cooling the mixture obtained in step (II) to 20° C. to 35° C.

When an acidic component such as an unneutralized fatty acid is present in the other components to be used, component (X) is consumed for neutralizing the negative charge, resulting in a risk of decreasing the content of component (X) in a free form in the resulting skin cleansing composition to a level lower than a predetermined amount. Accordingly, the step (II) is desirably a step for which the decrease is added. That is, the step (II) is preferably performed as step (II)' of sequentially mixing the components other than component (X) and mixing and stirring for dissolving each component before addition of component (X), subsequently adding a neutralizer to the mixture for neutralizing the acidic component, and then adding component (X) and mixing and stirring for dissolution, followed by step (III).

Alternatively, the acidic component may be directly neutralized with component (X) without using any neutralizer, unlike step (II)'. That is, the step (II) may be performed as step (II)" of sequentially mixing the components other than component (X) and mixing and stirring for dissolving each component before addition of component (X), adding component (X) for neutralizing the acidic component, and then mixing and stirring for dissolution, followed by step (III). In this case, the amount of component (X) added in step (II)" may be the sum of the content of component (X) in a free form in the resulting composition and the amount of component (X) necessary for neutralizing the acidic component.

Even in the case of preparing a skin cleansing composition containing both component (X) and component (Z), component (Z) is desirably treated as in component (X).

Regarding the above-described embodiments, the present invention further discloses the following skin cleansing composition.

[1] A skin cleansing composition comprising 0.08 mass % or more and 35 mass % or less of (X) 2-amino-2-methyl-1-propanol and having a pH of 9.3 or more and 12.5 or less at 25° C.

[2] The skin cleansing composition according to above [1], wherein the content of the component (X) is preferably 0.1 mass % or more, more preferably 0.5 mass % or more, further preferably 0.8 mass % or more, further preferably 1 mass % or more, further preferably 2 mass % or more, further preferably 3 mass % or more, further preferably 4 mass % or more, and further preferably 5 mass % or more; and preferably 30 mass % or less, more preferably 25 mass % or less, further preferably 20 mass % or less, further preferably 15 mass % or less, further preferably 12 mass % or less, further preferably 11 mass % or less, and further preferably 10 mass % or less.

[3] The skin cleansing composition according to above [1] or [2], wherein the mass ratio of the content of component (X) in a free form to the content of component (X), (content of free-form component (X))/(content of component (X)), is preferably 0.6 or more, more preferably 0.8 or more, further preferably 0.9 or more, and further preferably 1.0.

[4] The skin cleansing composition according to any one of above [1] to [3], further comprising (A) an anionic surfactant, wherein the content of component (A) is preferably 0.01 mass % or more, more preferably 0.02 mass % or more, further preferably 0.05 mass % or more, further preferably 0.1 mass % or more, further preferably 0.3 mass % or more, and further preferably 0.5 mass % or more; and preferably 30 mass % or less, more preferably 20 mass % or less, further preferably 15 mass % or less, further preferably 12 mass % or less, further preferably 10 mass % or less, further preferably 8 mass % or less, and further preferably 4 mass % or less.

[5] The skin cleansing composition according to above [4], wherein the component (A) comprises (A1) an anionic surfactant having a carboxylic acid group and/or (A2) an anionic surfactant having a sulfonic acid group or a sulfate group.

[6] The skin cleansing composition according to above [4] or [5], wherein the component (A1) preferably comprises one or more selected from the group consisting of a fatty acid having 10 to 22 carbon atoms or a salt thereof, an ether carboxylic acid or a salt thereof, and an N-acylamino acid salt; and the component (A2) preferably comprises one or more selected from the group consisting of an alkylbenzene sulfonic acid or a salt thereof, an alkanesulfonic acid or a salt thereof, an alkenylsulfonic acid or a salt thereof, an alkylsulfonic acid or a salt thereof, an acylisethionic acid or a salt thereof, an alkyl sulfate or a salt thereof, an alkyl ether sulfate or a salt thereof, an alkyl sulfosuccinic acid or a salt thereof, a sulfofatty acid methyl ester or a salt thereof, a fatty acid alkanolamide sulfate or a salt thereof, and a monoacylglycerol sulfate or a salt thereof.

[7] The skin cleansing composition according to any one of above [4] to [6], wherein the content of the component (A1) is preferably 0.01 mass % or more, more preferably 0.05 mass % or more, further preferably 0.10 mass % or more, and further preferably 0.3 mass % or more; and preferably 5 mass % or less, more preferably 3 mass % or less, further preferably 2.0 mass % or less, further preferably 1.5 mass % or less, and further preferably 1.0 mass % or less.

[8] The skin cleansing composition according to any one of above [4] to [7], wherein the content of the component (A2) is preferably 0.01 mass % or more, more preferably 0.03 mass % or more, further preferably 0.05 mass % or more, further preferably 0.10 mass % or more, further preferably 0.2 mass % or more, further preferably 0.3 mass % or more, and further preferably 0.5 mass % or more; and preferably 20 mass % or less, more preferably 18 mass % or less, further preferably 15 mass % or less, further preferably 12 mass % or less, further preferably 10 mass % or less, further preferably 8 mass % or less, further preferably 5 mass % or less, further preferably 4 mass % or less, and further preferably 3 mass % or less.

[9] The skin cleansing composition according to any one of above [4] to [8], wherein the mass ratio of the content of the component (X) to the content of the component (A1), (X)/(A1), is preferably 0.1 or more, more preferably 0.5 or more, further preferably 1.0 or more, further preferably 2 or more, further preferably 5 or more, and further preferably 8 or more; and preferably 100 or less, more preferably 80 or less, further preferably 70 or less, further preferably 60 or less, further preferably 50 or less, further preferably 40 or less, further preferably 30 or less, and further preferably 20 or less.

[10] The skin cleansing composition according to any one of above [4] to [9], wherein the mass ratio of the content of the component (X) to the content of the component (A2), (X)/(A2), is preferably 0.005 or more, more preferably 0.01 or more, further preferably 0.10 or more, more preferably 0.20 or more, further preferably 0.25 or more, further preferably 0.3 or more, and further preferably 0.5 or more; and preferably 100 or less, more preferably 60 or less, further preferably 50 or less, further preferably 40 or less, further preferably 30 or less, further preferably 20 or less, further preferably 15 or less, further preferably 14 or less, and further preferably 12.5 or less.

[11] The skin cleansing composition according to any one of above [1] to [10], wherein the content of the anionic surfactant other than the components (A1) and (A2) is preferably 0.01 mass % or more, more preferably 0.05 mass % or more, and further preferably 0.1 mass % or more; and preferably 10 mass % or less, more preferably 5 mass % or less, further preferably 1 mass % or less, and further preferably 0.5 mass % or less.

[12] The skin cleansing composition according to any one of above [1] to [11], further comprising (B) a nonionic surfactant and preferably comprising (B1) a nonionic surfactant having an HLB of 11 or more and/or (B2) a nonionic surfactant having an HLB of less than 11 as component (B).

[13] The skin cleansing composition according to above [12], wherein the component (B1) comprises preferably one or more selected from the group consisting of a polyglycerol fatty acid ester, a polyethylene glycol fatty acid ester, a polyoxyethylene alkyl ether, a polyoxyethylene glycerol fatty acid ester, a polyoxyethylene sorbitan fatty acid ester, a polyoxyethylene hydrogenated castor oil fatty acid ester, and an alkyl polyglucoside, and more preferably one or more selected from the group consisting of a polyethylene glycol fatty acid ester, a polyoxyethylene alkyl ether, a polyoxyethylene sorbitan fatty acid ester, and an alkyl polyglucoside.

[14] The skin cleansing composition according to above [12] or [13], wherein component (B2) preferably comprises one or more selected from the group consisting of a polyoxyethylene alkyl ether and a polyglycerol fatty acid ester.

[15] The skin cleansing composition according to any one of above [12] to [14], wherein the content of the component (B) is preferably 0.1 mass % or more, more preferably 0.4 mass % or more, and more preferably 0.5 mass % or more; and preferably 30 mass % or less, more preferably 25 mass % or less, further preferably 20 mass % or less, further preferably 15 mass % or less, and further preferably 10 mass % or less.

[16] The skin cleansing composition according to any one of above [12] to [15], wherein the mass ratio of the content of the component (B1) to the content of the component (B2), (B1)/(B2), is preferably 0.1 or more, more preferably 0.6 or more, further preferably 0.8 or more, further preferably 1.5 or more, further preferably 2.5 or more, and further preferably 5 or more; and preferably 25 or less, more preferably 20 or less, further preferably 16 or less, further preferably 14 or less, and further preferably 12 or less.

[17] The skin cleansing composition according to any one of above [12] to [16], wherein the mass ratio of the content of the component (X) to the content of the component (B), (X)/(B), is 0.01 or more, more preferably 0.02 or more, more preferably 0.03 or more, more preferably 0.1 or more, further preferably 0.3 or more, and further preferably 0.5 or more; and preferably 50 or less, more preferably 30 or less, further preferably 25 or less, further preferably 20 or less, and further preferably 15 or less.

[18] The skin cleansing composition according to any one of above [1] to [17], further comprising (C) an ampholytic surfactant, wherein the content of the component (C) is preferably 0.1 mass % or more, more preferably 0.5 mass % or more, and further preferably 1 mass % or more; and preferably 15 mass % or less, more preferably 10 mass % or less, and further preferably 5 mass % or less.

[19] The skin cleansing composition according to any one of above [1] to [18], further comprising (D) a polyol, wherein the content of the component (D) is preferably 0.5 mass % or more, more preferably 1 mass % or more, further preferably 3 mass % or more, further preferably 5 mass % or more, further preferably 8 mass % or more, and 10 mass % or more; and preferably 40 mass % or less, more preferably 35 mass % or less, further preferably 30 mass % or less, further preferably 25 mass % or less, and further preferably 20 mass % or less.

[20] The skin cleansing composition according to above [19], wherein the component (D) comprises preferably one or more selected from the group consisting of ethylene glycol, diethylene glycol, polyethylene glycol, propylene glycol, dipropylene glycol, polypropylene glycol, isoprene glycol, hexylene glycol, 1,3-butylene glycol, glycerol, diglycerol, triglycerol, tetraglycerol, hexaglycerol, decaglycerol, trimethyl propanol, erythritol, pentaerythritol, dipentaerythritol, glucose, mannose, galactose, sucrose, fructose, maltose, maltitol, xylitol, inositol, sorbitan, and sorbitol, and more preferably one or more selected from the group consisting of dipropylene glycol, 1,3-butylene glycol, glycerol, sorbitol, and mannitol.

[21] The skin cleansing composition according to any one of above [1] to [20], further comprising (E) a water-soluble polymer, wherein the content of the component (E) in the composition is preferably 0.01 mass % or more, more preferably 0.05 mass % or more, further preferably 0.10 mass % or more, and further preferably 0.15 mass % or more; and preferably 3 mass % or less, more preferably 2 mass % or less, further preferably 1 mass % or less, and further preferably 0.8 mass % or less.

[22] The skin cleansing composition according to above [21], wherein the component (E) comprises one or more selected from the group consisting of a carboxyvinyl polymer, an acrylic acid/alkyl (meth)acrylate copolymer, and cellulose to which a hydroxyethyl group or a hydroxypropyl group has been added.

[23] The skin cleansing composition according to any one of above [1] to [22], further comprising (F) one or more selected from the group consisting of a neutral amino acid, a betaine compound, and ethylenediamine tetraacetate, wherein the content of the component (F) in the composition is preferably 0.1 mass % or more, more preferably 0.5 mass % or more, and further preferably 1 mass % or more; and preferably 20 mass % or less, more preferably 15 mass % or less, and further preferably 10 mass % or less.

[24] The skin cleansing composition according to above [23], wherein the component (F) comprises preferably one or more selected from the group consisting of trimethyl glycine, trimethyl serine, hydroxyethyl dimethyl glycine, and monoethanol-CS-carboxybetaine, more preferably one or more selected from the group consisting of trimethyl glycine, trimethyl serine, and hydroxyethyl dimethyl glycine, and further preferably trimethyl glycine.

[25] The skin cleansing composition according to any one of above [1] to [24], comprising (G) water, wherein the content of the component (G) is preferably 10 mass % or more, more preferably 20 mass % or more, and further preferably 30 mass % or more; and preferably 99.9 mass % or less, more preferably 99.5 mass % or less, and further preferably 99 mass % or less.

[26] The skin cleansing composition according to any one of above [1] to [25], wherein the pH at 25° C. is preferably 9.5 or more, more preferably 9.8 or more, further preferably 10.0 or more, further preferably 10.2 or more, and further preferably 10.5 or more; and preferably 12.2 or less, further preferably 12.0 or less, further preferably 11.8 or less, and further preferably 11.5 or less.

[27] A skin cleansing composition comprising 0.08 mass % or more and 35 mass % or less of (X) 2-amino-2-methyl-1-propanol and (Z) one or two selected from the group consisting of 2-amino-2-hydroxymethyl-1,3-propanediol and 2-amino-2-methyl-1,3-propanediol, preferably 2-amino-2-methyl-1,3-propanediol, and having a pH of 8.3 or more and 12.5 or less at 25° C.

[28] The skin cleansing composition according to above [27], wherein the pH at 25° C. is preferably 8.5 or more, more preferably 8.8 or more, further preferably 9.0 or more, further preferably 9.2 or more, further preferably 9.5 or more, further preferably 9.8 or more, and further preferably 10.0 or more; and preferably 12.2 or less, more preferably 12.0 or less, further preferably 11.8 or less, further preferably 11.5 or less, further preferably 11.2 or less, and further preferably 11 or less.

[29] The skin cleansing composition according to above [27] or [28], wherein the content of the component (Z) is preferably 0.1 mass % or more, more preferably 0.5 mass % or more, further preferably 0.8 mass % or more, and further preferably 1 mass % or more; and preferably 15 mass % or less, more preferably 12 mass % or less, further preferably 11 mass % or less, and further preferably 10 mass % or less.

[30] The skin cleansing composition according to any one of above [27] to [29], wherein the mass ratio of the content of the component (Z) in a free form to the content of the component (Z), (content of free-form component (Z))/(content of component (Z)), is preferably 0.6 or more, more preferably 0.8 or more, further preferably 0.9 or more, and further preferably 1.0.

[31] The skin cleansing composition according to any one of above [27] to [30], wherein the mass ratio of the content of the component (X) to the content of the component (Z), (X)/(Z), is preferably 0.001 or more, more preferably 0.05 or more, further preferably 0.08 or more, and further preferably 0.1 or more; and preferably 100 or less, more preferably 50 or less, further preferably 20 or less, and further preferably 10 or less.

[32] The skin cleansing composition according to any one of above [27] to [31], wherein the total content of the component (X) and the component (Z) is preferably 0.08 mass % or more, more preferably 0.1 mass % or more, further preferably 0.5 mass % or more, further preferably 0.8 mass % or more, further preferably 1 mass % or more, further preferably 2 mass % or more, further preferably 3 mass % or more, further preferably 4 mass % or more, further preferably 5 mass % or more, and further preferably higher than 5 mass %; and preferably 35 mass % or less, more preferably 30 mass % or less, further preferably 25 mass % or less, further preferably 20 mass % or less, further preferably 15 mass % or less, further preferably 12 mass % or less, further preferably 11 mass % or less, and further preferably 10 mass % or less.

[33] The skin cleansing composition according to any one of above [1] to [32], wherein the skin cleansing composition is preferably in a foam, liquid, paste, or cream dosage form and more preferably in a foam or liquid dosage form.

[34] A method for producing the skin cleansing composition according to any one of above [1] to [33], the method comprising step (I) of heating water to 60° C. to 80° C. in advance, step (II) of sequentially adding the component (A) and other components as needed to the water obtained in step (I) and mixing and stirring, and step (III) of cooling the mixture obtained in step (II) to 20° C. to 35° C.

[35] The method for producing the skin cleansing composition according to above [34], wherein the skin cleansing composition comprises an acidic component, and the step (II) comprises step (II1) of sequentially mixing components comprising the acidic component, other than the component (X) and mixing and stirring for dissolving each component, step (II2) of subsequently adding a neutralizer to the mixture for neutralizing the acidic component, and step (II3) of subsequently adding the component (X) and the component (Z) as needed and mixing and stirring for dissolution.

[36] The method for producing the skin cleansing composition according to above [35], wherein the neutralizer is one or two selected from the group consisting of sodium hydroxide and potassium hydroxide.

[37] The method for producing the skin cleansing composition according to above [34], wherein the skin cleansing composition comprises an acidic component, and the step (II) comprises step (II1') of sequentially mixing components comprising the acidic component, other than the component (X), and mixing and stirring for dissolving each component and step (II2') of subsequently adding the component (X) in an amount higher than that necessary for neutralizing the acidic component and the component (Z) as needed and mixing and stirring for dissolution.

[38] A method for using the skin cleansing composition according to any one of above [1] to [33], comprising applying the skin cleansing composition according to any one of above [1] to [33] to preferably the skin of a body, more preferably the skin of, for example, the face, neck, limbs, or torso, excluding the scalp, further preferably the pore sites on the skin of these, and further preferably the pore sites on the skin from the forehead to the nose tip of the face; and, after a certain period of time, washing away the composition with water or wiping away the composition with a wiping material.

[39] The method for using the skin cleansing composition according to above [38], wherein the method comprising massaging the application site for 10 seconds to 10 minutes, preferably 15 seconds to 5 minutes, more preferably 30 seconds to 4 minutes, and further preferably 1 to 3 minutes; and sequentially washing away the composition remaining on the application site with water or wiping away with a wiping material.

[40] The skin cleansing composition according to any one of above [1] to [33], wherein the content of the component (X) is 1.5 mass % or more and 25 mass % or less, and the pH at 25° C. is 9.3 or more and 12.5 or less.

[41] The skin cleansing composition according to any one of above [1] to [33] and [40], wherein the content of the component (X) is 1 mass % or more and 15 mass % or less, and the pH at 25° C. is 9.3 or more and 12.5 or less.

[42] The skin cleansing composition according to any one of above [1] to [33], [40], and [41], wherein the content of the component (X) is 3 mass % or more and 11 mass % or less, and the pH at 25° C. is 9.3 or more and 12.5 or less.

[43] The skin cleansing composition according to any one of above [1] to [33] and [40] to [42], wherein the content of the component (X) is 5 mass % or more and 10 mass % or less, and the pH at 25° C. is 9.3 or more and 12.5 or less.

[44] The skin cleansing composition according to any one of above [1] to [33] and [40] to [43], the composition comprising the component (X) and (A) an anionic surfactant, wherein the content of the component (X) in the composition is 0.08 mass % or more and 35 mass % or less and the content of the component (A) is 0.01 mass % or more and 30 mass % or less, and the composition having a pH of 9.3 or more and 12.5 or less at 25° C.

[45] The skin cleansing composition according to any one of above [1] to [33] and [40] to [44], the composition comprising the component (X) and (A) an anionic surfactant, wherein the content of the component (X) in the composition is 0.1 mass % or more and 30 mass % or less and the content of the component (A) is 0.02 mass % or more and 20 mass % or less, and the composition having a pH of 9.3 or more and 12.5 or less at 25° C.

[46] The skin cleansing composition according to any one of above [1] to [33] and [40] to [45], the composition comprising component (X) and (A) an anionic surfactant, wherein the content of the component (X) in the composition is 0.5 mass % or more and 25 mass % or less and the content of the component (A) is 0.1 mass % or more and 15 mass % or less, and the composition having a pH of 9.3 or more and 12.5 or less at 25° C.

[47] The skin cleansing composition according to any one of above [1] to [33] and [40] to [46], the composition comprising the component (X) and (A1) an anionic surfactant having a carboxylic acid group and/or (A2) an anionic surfactant having a sulfonic acid group or a sulfate group, wherein the content of the component (X) in the composition is 0.5 mass % or more and 25 mass % or less and the content of the component (A) is 0.1 mass % or more and 15 mass % or less, and the composition having a pH of 9.3 or more and 12.5 or less at 25° C.

[48] The skin cleansing composition according to any one of above [1] to [33] and [40] to [47], the composition comprising the component (X) and (A1) an anionic surfactant having a carboxylic acid group, wherein the content of the component (X) in the composition is 0.08 mass % or more and 35 mass % or less, the content of the component (A1) is 0.01 mass % or more and 5 mass % or less, and the mass ratio of the content of the component (X) to the content of the component (A1), (X)/(A1), is 0.1 or more and 100 or less, and the composition having a pH of 9.3 or more and 12.5 or less at 25° C.

[49] The skin cleansing composition according to any one of above [1] to [33] and [40] to [48], the composition comprising the component (X) and (A1) an anionic surfactant having a carboxylic acid group, wherein the content of the component (X) in the composition is 0.1 mass % or more and 30 mass % or less, the content of the component (A1) is 0.05 mass % or more and 3 mass % or less, and the mass ratio of the content of the component (X) to the content of the component (A1), (X)/(A1), is 0.5 or more and 80 or less, and the composition having a pH of 9.3 or more and 12.5 or less at 25° C.

[50] The skin cleansing composition according to any one of above [1] to [33] and [40] to [49], the composition comprising the component (X) and (A1) an anionic surfactant having a carboxylic acid group, where the content of the component (X) in the composition is 0.5 mass % or more and 25 mass % or less, the content of the component (A1) is 0.05 mass % or more and 2.0 mass % or less, and the mass ratio of the content of the component (X) to the content of the component (A1), (X)/(A1), is 1.0 or more and 50 or less, and the composition having a pH of 9.3 or more and 12.5 or less at 25° C.

[51] The skin cleansing composition according to any one of above [1] to [33] and [40] to [50], the composition comprising the component (X) and (A1) an anionic surfactant having a carboxylic acid group selected from the group consisting of a fatty acid or a salt thereof, an ether carboxylic acid or a salt thereof, and an N-acylamino acid salt, wherein the content of the component (X) in the composition is 0.5 mass % or more and 25 mass % or less, the content of the component (A1) is 0.1 mass % or more and 2.0 mass % or less, and the mass ratio of the content of the component (X) to the content of the component (A1), (X)/(A1), is 1.0 or more and 50 or less, and the composition having a pH of 9.3 or more and 12.5 or less at 25° C.

[52] The skin cleansing composition according to any one of above [1] to [33] and [40] to [51], the composition comprising the component (X) and (A2) an anionic surfactant having a sulfonic acid group or a sulfate group, wherein the content of the component (X) in the composition is 0.08 mass % or more and 35 mass % or less, the content of the component (A2) is 0.01 mass % or more and 20 mass % or less, and the mass ratio of the content of the component (X) to the content of the component (A2), (X)/(A2), is 0.005 or more and 100 or less, and the composition having a pH of 9.3 or more and 12.5 or less at 25° C.

[53] The skin cleansing composition according to any one of above [1] to [33] and [40] to [52], the composition comprising the component (X) and (A2) an anionic surfactant having a sulfonic acid group or a sulfate group, wherein the content of the component (X) in the composition is 1 mass % or more and 20 mass % or less, the content of the component (A2) is 0.03 mass % or more and 18 mass % or less, and the mass ratio of the content of the component (X) to the content of the component (A2), (X)/(A2), is 0.01 or more and 60 or less, and the composition having a pH of 9.3 or more and 12.5 or less at 25° C.

[54] The skin cleansing composition according to any one of above [1] to [33] and [40] to [53], the composition comprising the component (X) and (A2) an anionic surfactant having a sulfonic acid group or a sulfate group, wherein the content of the component (X) in the composition is 0.5 mass % or more and 25 mass % or less, the content of the component (A2) is 0.10 mass % or more and 15 mass % or less, and the mass ratio of the content of the component (X) to the content of the component (A2), (X)/(A2), is 0.10 or more and 50 or less, and the composition having a pH of 9.3 or more and 12.5 or less at 25° C.

[55] The skin cleansing composition according to any one of above [1] to [33] and [40] to [54], the composition comprising the component (X) and (A2) an anionic surfactant having a sulfonic acid group or a sulfate group selected from the group consisting of an alkylbenzene sulfonic acid or a salt thereof, an acylisethionic acid or a salt thereof, an alkyl sulfate or a salt thereof, an alkyl ether sulfate or a salt thereof, an alkenylsulfonic acid or a salt thereof, and an alkylsulfonic acid or a salt thereof, wherein the content of the component (X) in the composition is 0.5 mass % or more and 25 mass % or less, the content of the component (A2) is 0.5 mass % or more and 15 mass % or less, and the mass ratio of the content of the component (X) to the content of the component (A2), (X)/(A2), is 0.10 or more and 50 or less, and the composition having a pH of 9.3 or more and 12.5 or less at 25° C.

[56] The skin cleansing composition according to any one of above [1] to [33] and [40] to [55], the composition comprising the component (X) and (B) a nonionic surfactant, wherein the content of the component (X) in the composition is 0.08 mass % or more and 35 mass % or less and the content of the component (B) is 0.1 mass % or more and 30 mass % or less, and the composition having a pH of 9.3 or more and 12.5 or less at 25° C.

[57] The skin cleansing composition according to any one of above [1] to [33] and [40] to [56], the composition comprising the component (X) and (B) a nonionic surfactant, wherein the content of the component (X) in the composition is 0.1 mass % or more and 30 mass % or less and the content of the component (B) is 0.4 mass % or more and 25 mass % or less, and the composition having a pH of 9.3 or more and 12.5 or less at 25° C.

[58] The skin cleansing composition according to any one of above [1] to [33] and [40] to [57], the composition comprising the component (X) and (B) a nonionic surfactant, wherein the content of the component (X) in the composition is 0.5 mass % or more and 25 mass % or less and the content of the component (B) is 0.5 mass % or more and 15 mass % or less, and the composition having a pH of 9.3 or more and 12.5 or less at 25° C.

[59] The skin cleansing composition according to any one of above [1] to [33] and [40] to [58], the composition comprising the component (X) and (B) one or more nonionic surfactants selected from the group consisting of a polyglycerol fatty acid ester, a polyethylene glycol fatty acid ester, a polyoxyethylene glycerol fatty acid ester, a polyoxyethylene sorbitan fatty acid ester, a polyoxyethylene hydrogenated castor oil fatty acid ester, a polyoxyethylene alkyl ether, and an alkyl polyglucoside, wherein the content of the component (X) in the composition is 0.5 mass % or more and 25 mass % or less and the content of the component (B) is 0.5 mass % or more and 15 mass % or less, and the composition having a pH of 9.3 or more and 12.5 or less at 25° C.

[60] The skin cleansing composition according to any one of above [1] to [33] and [40] to [59], the composition comprising the component (X) and (B) a nonionic surfactant, wherein the content of the component (X) in the composition is 0.08 mass % or more and 35 mass % or less, the content of the component (B) is 0.1 mass % or more and 30 mass % or less, and the mass ratio of the content of the component (X) to the content of the component (B), (X)/(B), is 0.01 or more and 50 or less, and the composition having a pH of 9.3 or more and 12.5 or less at 25° C.

[61] The skin cleansing composition according to any one of above [1] to [33] and [40] to [60], the composition comprising the component (X) and (B) a nonionic surfactant, wherein the content of the component (X) in the composition is 0.1 mass % or more and 30 mass % or less, the content of the component (B) is 0.4 mass % or more and 25 mass % or less, and the mass ratio of the content of the component (X) to the content of the component (B), (X)/(B), is 0.02 or more and 30 or less, and the composition having a pH of 9.3 or more and 12.5 or less at 25° C.

[62] The skin cleansing composition according to any one of above [1] to [33] and [40] to [61], the composition comprising the component (X) and (B) a nonionic surfactant, wherein the content of the component (X) in the composition is 0.5 mass % or more and 25 mass % or less, the content of the component (B) is 0.5 mass % or more and 15 mass % or less, and the mass ratio of the content of the component (X) to the content of the component (B), (X)/(B), is 0.1 or more and 30 or less, and the composition having a pH of 9.3 or more and 12.5 or less at 25° C.

[63] The skin cleansing composition according to any one of above [1] to [33] and [40] to [62], the composition comprising the component (X) and (B) one or more nonionic surfactants selected from the group consisting of a polyglycerol fatty acid ester, a polyethylene glycol fatty acid ester, a polyoxyethylene glycerol fatty acid ester, a polyoxyethylene sorbitan fatty acid ester, a polyoxyethylene hydrogenated castor oil fatty acid ester, a polyoxyethylene alkyl ether, and an alkyl polyglucoside, wherein the content of the component (X) in the composition is 0.5 mass % or more and 25 mass % or less, the content of the component (B) is 0.5 mass % or more and 15 mass % or less, and the mass ratio of the content of the component (X) to the content of the component (B), (X)/(B), is 0.1 or more and 30 or less, and the composition having a pH of 9.3 or more and 12.5 or less at 25° C.

EXAMPLES

The present invention will now be specifically described based on Examples. Unless otherwise indicated in the table, the content of each component is represented by "mass %" (only sodium cocoyl glutamate as component (A1) is shown in terms of acid equivalent).

Samples were prepared according to the formulations shown in Tables 1 to 7. Specifically, each sample can be prepared by heating water to 70° C. in advance, sequentially adding all remaining components to the water, mixing them by stirring, and cooling the resulting mixture to 25° C. Tables 1 to 7 also show the results.

The pH of each of the resulting skin cleansing compositions was measured at 25° C. with a pH meter (manufactured by HORIBA, Ltd., Model No. F-22).

«Evaluation of Detergency Against Keratotic Plug»

1. Evaluation of Detergency Against Keratotic Plug during Cleansing

Keratotic plugs in the nasal region were removed with "Biore Nose Pack (manufactured by Kao Corporation)", the resulting keratotic plugs on the pack were gently taken out with tweezers.

The resulting keratotic plugs were placed on a slide glass and were covered with a cover glass, and 0.05 mL of a sample was dropwise added to an edge of the cover glass. Consequently, the sample entered into the gap between the slide glass and the cover glass by capillary phenomenon and was brought into contact with the keratotic plugs. The contact of the keratotic plugs and the sample was recorded with a digital microscope (VHX-5000, manufactured by Keyence Corporation, magnification: 150×), and the penetration of the sample into the keratotic plugs and the collapse state of the keratotic plugs were evaluated after one minute from the contact of the keratotic plugs with the sample. The results of each evaluation are shown in the columns "Keratotic plug detergency (penetration)" and "Keratotic plug detergency (during cleansing)" in Tables. The measurements were performed at 25° C.

The penetration was relatively evaluated by criteria with 11 ratings starting from the rating 1 "the sample hardly penetrated into the keratotic plug" to the rating 11 "the sample penetrated to the center of the keratotic plug". The collapsibility by the detergency against keratotic plug was relatively evaluated by criteria with 11 ratings starting from the rating 1 "almost no change is observed in the external appearance of the keratotic plug" to the rating 11 "peeling or separation is observed in the area from the surface layer to the central portion of the keratotic plug (the initial appearance of the keratotic plug is not retained)".

2. Evaluation of Detergency Against Keratotic Plug After Washing with Water

After one minute from the contact of the keratotic plugs with the sample, Kimwipes (registered trademark) was brought into contact with an edge of the cover glass to remove the sample under the cover glass. Then, 0.05 mL of water was gradually dropwise added to an edge of the cover glass. The sample dropwise added with water was recorded with the digital microscope, and the collapse state of the keratotic plugs was evaluated after one minute from the contact of the keratotic plugs with water according to the criteria for evaluating collapsibility of the keratotic plugs. The results of the evaluation are shown in the column "Keratotic plug detergency (during washing with water)" in Table. The measurements were performed at 25° C.

«Evaluation of Effect of Suppressing Protein Aggregation»

Thirty milliliters of a sample and 0.06 g of an insoluble protein (seine protein) were placed in a 35-mL standard glass bottle, and the concentration of the insoluble protein was adjusted to 0.2 mass % (test sample). Separately, a standard sample was prepared by using water instead of the sample and adjusting the concentration of the insoluble protein to 0.2 mass %. Subsequently, the standard glass bottles were sufficiently shaken and stirred up and down (shake width: 15 cm, 20 times at a rate of 5 times for 3 seconds) in a thermostatic chamber of 25° C. and were left to stand for 3 minutes. The precipitation state of the insoluble protein was then visually verified, and the ratio of the amount of the precipitated standard sample to the amount of the precipitated test sample (the height of the precipitate in each standard glass bottle was measured as the precipitation amount), (precipitation amount of standard sample)/(precipitation amount of test sample), was calculated. A higher ratio indicates a higher effect of suppressing protein aggregation.

«Evaluation of Skin Irritation»

Two expert panelists dropwise applied 0.1 mL of each sample to the palm and massaged the palm for 10 seconds. The sliminess of the skin during the massage was evaluated according to the following criteria. The results of evaluation are each expressed by the average of the results evaluated by the two expert panelists. Higher sliminess indicates higher dissolution of the horny layer and higher skin irritation.

(Criteria)

3: Sense of strong sliminess;
2: Sense of slight sliminess;
1: No sense of sliminess.

«Evaluation of Softness of Skin»

Two expert panelists uniformly applied 1 mL of each sample to the face and massaged the face with hands for 30 seconds. Subsequently, the face was rinsed with tap water (amount of rinse water: 1000 mL for 10 seconds, water temperature: 25° C. to 30° C.) for 30 seconds. After the rinsing, the moisture was wiped off with a towel, and the softness of the skin after 20 minutes was evaluated according to the following criteria. The results of evaluation are each expressed by the average of the results evaluated by the two expert panelists.

The sample caused skin irritation when applied was not subjected to the test for evaluating softening the skin. The sample not subjected to the evaluation is indicated by "-" in the column of the result of evaluation.

(Criteria)
  4: Very soft,
  3: Slightly soft,
  2: Slightly stretched,
  1: Very stretched.

«Evaluation of Foaming Properties»

Two expert panelists dropwise applied 1 mL of each sample onto a previously wetted hand and rubbed the palms of both hands for 10 seconds to foam the sample, followed by evaluation according to the following criteria. The results of evaluation are each expressed by the average of the results evaluated by the two expert panelists.

(Criteria)
  4: Highly foamed,
  3: Moderately foamed,
  2: Slightly foamed,
  1: Hardly foamed,
  0: Not foamed.

«Evaluation of Sebum Cleansing Ability»

Carbon black was dispersed in an amount of 5 mass % in 95 mass % of the model sebum shown below for coloring, and the dispersion was melted at 50° C. and then applied to the inside of a forearm in a size of 3 cm in diameter (application quantity of model sebum: about 0.26 mg/cm$^2$). After the application, the model sebum was left to stand for 15 minutes to dry, and 1.0 mL of a sample was applied thereon, followed by massage for 30 seconds. The application site was rinsed with tap water (amount of rinse water: 1000 mL for 10 seconds, water temperature: 25° C. to 30° C.) for 30 seconds. The amount of the model sebum remaining on the skin after the rinsing was visually verified, and the sebum cleansing ability was evaluated according to the following criteria.

(Model Sebum)

| Component | mass % |
|---|---|
| Squalene | 9.0 |
| Myristyl myristate | 24.9 |
| Cotton seed oil | 47.0 |
| Cholesterol | 2.0 |
| Cholesteryl palmitate | 2.0 |
| Lauric acid | 0.2 |
| Myristic acid | 2.5 |
| Palmitic acid | 6.0 |
| Stearic acid | 0.9 |
| Oleic acid | 6.4 |
| Total | 100 |

(Criteria)
  5: The boundary between the model sebum-application site and the non-application site is not observed at all.
  4: A part of the boundary between the model sebum-application site and the non-application site is slightly observed.
  3: The entire boundary between the model sebum-application site and the non-application site is very slightly observed.
  2: The entire boundary between the model sebum-application site and the non-application site is slightly observed.
  1: The entire boundary between the model sebum-application site and the non-application site is clearly observed.

«Evaluation of Makeup Removability»

A foundation (SOFINA Primavista (registered trademark) liquid foundation ochre 05, manufactured by Kao Corporation) was uniformly applied to the inside of a forearm in a size of 3 cm in diameter and was dried for 15 minutes. Onto the foundation application site, 1.0 mL of a sample was applied, followed by massage for 30 seconds. The application site was rinsed with tap water (amount of rinse water: 1000 mL for 10 seconds, water temperature: 25° C. to 30° C.) for 30 seconds. The amount of the foundation remaining on the skin after the rinsing was visually verified for evaluation according to the following criteria.

(Criteria)
  5: The boundary between the foundation-application site and the non-application site is not observed at all.
  4: A part of the boundary between the foundation-application site and the non-application site is slightly observed.
  3: The entire boundary between the foundation-application site and the non-application site is very slightly observed.
  2: The entire boundary between the foundation-application site and the non-application site is slightly observed.
  1: The entire boundary between the foundation-application site and the non-application site is clearly observed.

TABLE 1

| | | | Test Example x2-1 | Test Example r-1 | Test Example r-2 | Test Example r-3 | Test Example r-4 |
|---|---|---|---|---|---|---|---|
| (X) | (X2) | AMP | 5 | | | | |
| | | POE (2) Na lauryl sulfate *[1] | | 5 | | | |
| | | Disodium hydrogen phosphate | | | 5 | | |
| | | Trisodium phosphate | | | | 5 | |
| | | Sodium hydrogen carbonate | | | | | 5 |
| | | 1M hydrochloric acid | 20 | | | 15 | |
| | | 1M sodium hydroxide | | | 0.3 | | 24 |
| | | Water (making up the balance) | 75 | 95 | 94.7 | 80 | 71 |
| | | Total | 100 | 100 | 100 | 100 | 100 |
| | | pH | 10 | 10 | 9.8 | 9.6 | 9.4 |
| Keratotic plug detergency (penetration) | | | 5 | 1 | 2 | 1 | 2 |
| Keratotic plug detergency (during cleansing) | | | 5 | 1 | 2 | 1 | 2 |
| Keratotic plug detergency (after washing with water) | | | 8 | 1 | 2 | 1 | 2 |
| Protein aggregation-suppressing effect | | | 10 | unmeasurable (dissolution) | 10 | 3 | 2.5 |

As obvious from the results of Table 1, when keratotic plugs were kept in contact with a sample for 1 minute, POE (2) sodium lauryl sulfate, which is an anionic surfactant usually used in skin cleansing compositions, hardly penetrated into the keratotic plugs, and the collapse of the keratotic plugs did not progress even if keratotic plugs were in contact with the sample (assumption of cleansing). The detergency against keratotic plug was hardly expressed. Furthermore, the action on proteins was strong to dissolve the proteins.

In AMP, the sample penetrated into keratotic plugs. In contrast, in disodium hydrogen phosphate, trisodium phosphate, and sodium hydrogen carbonate, which are also weak bases, the sample hardly penetrated into keratotic plugs. Accordingly, the collapse of the keratotic plugs did not progress even if the keratotic plugs were in contact with the sample (assumption of cleansing), and the detergency against keratotic plug was hardly expressed.

Furthermore, in AMP, the sample was washed away during washing with water, and the keratotic plugs swelled when the sample was substituted with water to cause a phenomenon of further accelerating the collapse of keratotic plugs. In contrast, in disodium hydrogen phosphate, trisodium phosphate, and sodium hydrogen carbonate, since the sample hardly penetrated into keratotic plugs, the keratotic plugs did not swell even during washing with water, and the collapse of keratotic plugs did not progress.

Accordingly, in order to accelerate the collapse of keratotic plugs during washing with water and to remove keratotic plugs from pores, it is preferable that the score of the detergency against keratotic plug during cleansing be 3 or more. More specifically, when the score of the detergency against keratotic plug during cleansing is 5 or more, the collapse of keratotic plugs during washing with water is accelerated, and keratotic plugs can be removed more quickly.

TABLE 2

|  |  |  | Test Example x2-1 | Test Example x2-2 | Test Example x2-3 | Test Example x2-4 | Test Example x2-5 | Test Example x2-6 | Test Example x2-7 |
|---|---|---|---|---|---|---|---|---|---|
| (X) | (X2) | AMP | 5 | 0.5 | 1 | 10 | 20 | 30 | 5 |
|  |  | 1M hydrochloric acid | 20 | 2 | 4 | 40 | 80 | 70 | 49 |
|  |  | 1M sodium hydroxide |  |  |  |  |  |  |  |
|  |  | Water (making up the balance) | 75 | 97.5 | 95 | 50 | 0 | 0 | 95 |
|  |  | Total | 100 | 100 | 100 | 100 | 100 | 100 | 100 |
|  |  | pH | 10 | 10 | 10 | 10 | 9.8 | 10 | 9 |
| Keratotic plug detergency (during cleansing) |  |  | 5 | 3 | 4 | 5 | 5 | 3 | 3 |
| Skin irritation |  |  | 1 | 1 | 1 | 1 | 1 | 1 | 1 |

|  |  |  | Test Example x2-8 | Test Example x2-9 | Test Example x2-10 | Test Example x2-11 | Test Example x2-12 | Test Example x2-13 |
|---|---|---|---|---|---|---|---|---|
| (X) | (X2) | AMP | 5 | 5 | 10 | 0.05 | 5 | 5 |
|  |  | 1M hydrochloric acid | 16 |  | 40 | 0.2 | 56 |  |
|  |  | 1M sodium hydroxide |  |  |  |  |  | 12 |
|  |  | Water (making up the balance) | 95 | 95 | 90 | 99.75 | 39 | 83 |
|  |  | Total | 100 | 100 | 100 | 100 | 100 | 100 |
|  |  | pH | 11 | 11.9 | 12 | 10 | 8 | 12.9 |
| Keratotic plug detergency (during cleansing) |  |  | 7 | 9 | 11 | 1 | 1 | 11 |
| Skin irritation |  |  | 1 | 2 | 2 | 1 | 1 | 3 |

TABLE 3

|  |  |  | Test Example x2x-1 | Test Example x2x-2 | Test Example x2x-3 | Test Example x2x-4 | Test Example x2x-5 | Test Example x2x-6 | Test Example x2x-7 |
|---|---|---|---|---|---|---|---|---|---|
| (X) | (X2) | AMP | 5 | 5 | 9 | 1 | 9 | 1 | 5 |
| (Z) | (X1) | Tris | 5 |  |  | 1 | 9 |  | 5 |
|  | (X3) | AMPD |  | 5 |  |  | 1 | 9 | 5 |
|  |  | 1M hydrochloric acid | 20.915 | 24.3 | 36.2 | 5.6 | 36.87 | 11.6 | 18 |
|  |  | 1M sodium hydroxide |  |  |  |  |  |  |  |

TABLE 3-continued

|  | Test Example x2x-1 | Test Example x2x-2 | Test Example x2x-3 | Test Example x2x-4 | Test Example x2x-5 | Test Example x2x-6 | Test Example x2x-7 |
|---|---|---|---|---|---|---|---|
| Water (making up the balance) | 74.085 | 70.7 | 62.8 | 85.4 | 62.13 | 79.4 | 72 |
| Total | 100 | 100 | 100 | 100 | 100 | 100 | 100 |
| pH | 10 | 10 | 10 | 10 | 10 | 10 | 10 |
| (X)/(Z) | 1.00 | 1.00 | 9.00 | 0.11 | 9.00 | 0.11 | 0.50 |
| Keratotic plug detergency (during cleansing) | 9 | 7 | 5 | 9 | 3 | 5 | 10 |

TABLE 4

|  |  |  | Test Example x2a1-1 | Test Example x2a1-2 | Test Example x2a1-3 | Test Example x2a1-4 | Test Example x2a1-5 | Test Example x2a1-6 | Test Example x2a1-7 | Test Example x2a1-8 | Test Example x2-1 |
|---|---|---|---|---|---|---|---|---|---|---|---|
| (X) | (X2) |  | AMP | 5 | 5 | 5 | 5 | 0.5 | 25 | 5 | 5 | 5 |
| (A) | (A1) |  | Lauric acid | 0.5 |  |  |  | 0.5 | 0.5 | 0.1 | 3 |  |
|  |  | Fatty acid mixture *2 |  | 0.6 |  |  |  |  |  |  |  |
|  |  | Na cocoyl glutamate |  |  | 0.5 |  |  |  |  |  |  |
|  |  | POE (4.5) lauryl ether acetate *3 |  |  |  | 0.5 |  |  |  |  |  |
|  |  | 1M hydrochloric acid | 16 | 16 | 18 | 18 | 1 | 40 | 18 | 10 |  |
|  |  | 1M sodium hydroxide |  |  |  |  |  |  |  |  | 20 |
|  |  | Water (making up the balance) | 78.5 | 78.4 | 76.5 | 76.5 | 98 | 34.5 | 76.9 | 82 | 75 |
|  |  | Total | 100 | 100 | 100 | 100 | 100 | 100 | 100 | 100 | 100 |
|  |  | pH | 10 | 10 | 10.1 | 10.1 | 10 | 10 | 10 | 10 | 10 |
|  |  | (X)/(A1) | 10.00 | 8.33 | 10.00 | 10.00 | 1.00 | 50.00 | 50.00 | 1.67 | — |
| Keratotic plug detergency (during cleansing) |  |  | 5 | 7 | 9 | 7 | 5 | 5 | 5 | 5 | 5 |
| Foaming property |  |  | 2 | 2 | 1.5 | 3 | 2 | 3 | 1.5 | 1.5 | 0 |

TABLE 5

|  |  |  | Test Example x2a2-1 | Test Example x2a2-2 | Test Example x2a2-3 | Test Example x2a2-4 | Test Example x2a2-5 | Test Example x2a2-6 | Test Example x2a2-7 | Test Example x2a2-8 | Test Example x2a2-9 | Test Example x2-1 |
|---|---|---|---|---|---|---|---|---|---|---|---|---|
| (X) | (X2) |  | AMP | 5 | 5 | 5 | 0.5 | 25 | 5 | 5 | 5 | 0.1 | 1 |
| (A) | (A2) |  | POE (2) Na lauryl sulfate *1 | 2 |  |  | 2 | 2 | 0.1 | 0.5 | 5 | 15 |  |
|  |  | Na lauryl sulfate *4 |  | 2 |  |  |  |  |  |  |  |  |
|  |  | IOS *5 |  |  | 2 |  |  |  |  |  |  |  |
|  |  | 1M hydrochloric acid | 18 | 20 | 20 | 2.4 |  | 18 | 20 | 22 | 0.2 | 4 |
|  |  | 1M sodium hydroxide |  |  |  |  |  |  |  |  |  |  |
|  |  | Water (making up the balance) | 75 | 73 | 73 | 95.1 | 73 | 76.9 | 74.5 | 68 | 84.7 | 95 |
|  |  | Total | 100 | 100 | 100 | 100 | 100 | 100 | 100 | 100 | 100 | 100 |
|  |  | pH | 10.1 | 10 | 10 | 10 | 10.2 | 10 | 10 | 10 | 10.3 | 10 |
|  |  | (X)/(A2) | 2.50 | 2.50 | 2.50 | 0.25 | 12.50 | 50.00 | 10.00 | 1.00 | 0.01 | — |
| Keratotic plug detergency (during cleansing) |  |  | 9 | 9 | 9 | 5 | 7 | 7 | 9 | 7 | 3 | 4 |
| Foaming properties |  |  | 3 | 4 | 2 | 2 | 2 | 2 | 2.5 | 3 | 3.5 | 0 |

TABLE 6

|  |  |  | Test Example x2b-1 | Test Example x2b-2 | Test Example x2b-3 | Test Example x2b-4 | Test Example x2b-5 | Test Example x2b-6 | Test Example x2-2 |
|---|---|---|---|---|---|---|---|---|---|
| (X) | (X2) | AMP | 0.5 | 0.5 | 5 | 5 | 5 | 25 | 0.5 |
| (B) | (B1) | POE (21) lauryl ether (HLB 16.6) *6 | 1 | 15 | 0.5 | 1 |  | 1 |  |
|  |  | Polyethylene glycol monolaurate (12 E.O.) (HLB 13.7) *7 |  |  |  |  | 15 |  |  |
|  |  | 1M hydrochloric acid 1M sodium hydroxide | 2 |  | 20 | 20 | 6 | 74 | 2 |
|  |  | Water (making up the balance) | 96.5 | 84.5 | 74.5 | 74 | 74 | 0 | 97.5 |
|  |  | Total | 100 | 100 | 100 | 100 | 100 | 100 | 100 |
|  |  | pH | 10 | 10.3 | 10 | 10 | 10.3 | 10 | 10 |
|  |  | (X)/(B) | 0.50 | 0.03 | 10.00 | 5.00 | 0.33 | 25.00 | — |
| Keratotic plug detergency (during cleansing) |  |  | 7 | 5 | 9 | 7 | 5 | 5 | 3 |
| Sebum detergency |  |  | 4 | 4.5 | 4.5 | 4.5 | 4.5 | 5 | 3 |

TABLE 7

|  |  |  | Test Example x2b-4 | Test Example x2b-7 |
|---|---|---|---|---|
| (X) | (X2) | AMP | 5 | 5 |
| (B) | (B1) | POE (21) lauryl ether (HLB 16.6) *6 | 1 |  |
|  |  | Polyethylene glycol monolaurate (12 E.O.) (HLB 13.7) *7 |  | 1 |
|  |  | Alkyl glucoside (HLB 15.7) *8 |  | 0.1 |
|  | (B2) | Polyglyceryl-2 isostearate (HLB 8.0) *9 |  | 0.1 |
|  |  | 1M hydrochloric acid | 20 | 20 |
|  |  | Water (making up the balance) | 74 | 73.8 |
|  |  | Total | 100 | 100 |
|  |  | pH | 10 | 10 |
|  |  | (X)/(B) | 5.00 | 4.17 |
|  |  | (B1)/(B2) | — | 11.00 |
| Keratotic plug detergency (during cleansing) |  |  | 7 | 9 |
| Makeup removability |  |  | 2 | 4 |

1: Lauric acid/myristic acid/palmitic acid/stearic acid=1/3/1/1 (parts by mass)
2: KAO AKIPO RLM-45 (manufactured by Kao Corporation)
3: EMAL 227 (manufactured by Kao Corporation)
4: EMAL 10PT (manufactured by Kao Corporation)
5: Internal olefin sulfonate composition in Production Example 7 in JP-A-2015-28123
6: EMULGEN 121 (manufactured by Kao Corporation)
7: EMANON 1112 (manufactured by Kao Corporation)
8: MYDOL 10 (manufactured by Kao Corporation)
9: COSMOL 41V (manufactured by The Nisshin OilliO Group, Ltd.)

Examples of the formulation of the present invention are shown below. All of them have effects equivalent to those of Examples described above.

Formulation Example 1

Facial Cleanser

| Component | Formulation Example 1 |
|---|---|
| 2-Amino-2-methyl-1-propanol | 5 |
| 2-Amino-2-hydroxymethyl-1,3-propanediol | 5 |
| POE (2) sodium lauryl sulfate *1 | 1.0 |
| Sodium cocoyl glutamate | 1 |
| Lauramidopropyl betaine *10 | 0.5 |
| Glycerol | 5 |
| 1,3-Butylene glycol | 5 |
| Hydroxyethyl cellulose *11 | 0.1 |
| (Acrylate/alkyl (C10-30) acrylate) crosspolymer *12 | 0.1 |
| 50% Aqueous solution of malic acid | 2 |
| Water | 70.7 |
| pH | 10 |
| Keratotic plug detergency | 3 |

Formulation Example 2

Body Cleanser

| Component |  |
|---|---|
| 2-Amino-2-methyl-1-propanol | 5 |
| Arginine | 5 |
| POE (21) lauryl ether *6 | 0.25 |
| Myristic acid | 0.4 |
| POE (2.6) lauryl ether acetate *13 | 0.1 |
| Trehalose | 5 |
| Sorbitol | 3.9 |
| Mannitol | 10 |
| Water | 70.35 |
| pH | 10 |
| Keratotic plug detergency | 9 |

10: Amphitol 20IID (manufactured by Kao Corporation)
11: HEC Daicel SE850 (manufactured by Daicel Fine-Chem Ltd.)
12: Carbopol Ultrez 21 polymer (manufactured by Lubrizol Advanced Materials, Inc.)
13: AKYPO LM 26C (manufactured by Kao Corporation)

The invention claimed is:

1. A skin cleansing composition comprising 1 to 25 mass % of (X) 2-amino-2-methyl-1-propanol and having a pH of 9.5 or more and 12.5 or less at 25° C., wherein said composition does not contain more than 3 mass % of a surfactant of Formula (1):

$R^1O(CH_2CH_2O)_mCH_2COOM^1$, wherein $R^1$ represents an alkyl or alkenyl group having 10 to 22 carbon atoms; m represents a number of 0.5 to 10 on average; and $M^1$ represents a hydrogen atom, an alkali metal, an alkaline earth metal, ammonium, or organic ammonium.

2. The skin cleansing composition according to claim 1, further comprising (A) an anionic surfactant.

3. The skin cleansing composition according to claim 2, Therein the component (A) comprises (A1) an anionic surfactant having a carboxylic acid group and/or (A2) an anionic surfactant having a sulfonic acid group or a sulfate group.

4. The skin cleansing composition according to claim 3, wherein a mass ratio of a content of the component (X) to a content of the component (A1), (X)/(A1), is 1 or more and 100 or less.

5. The skin cleansing composition according to claim 3, wherein a mass ratio of a content of the component (X) to a content of the component (A2), (X)/(A2), is 0.1 or more and 100 or less.

6. The skin cleansing composition according to claim 1, further comprising (B) a nonionic surfactant.

7. The skin cleansing composition according to claim 6, wherein the component (B) comprises (B1) a nonionic surfactant having an HLB of 11 or more and/or (B2) a nonionic surfactant having an HLB of less than 11.

8. A skin cleansing composition comprising 0.5 to 10 mass % of (X) 2amino-2-methyl-1-propanol, and 0.5 to 12 mass % of (Z) at least one member selected from the group consisting of 2-amino-2-hydroxymethyl-1,3-propanediol and 2-amino-2-methyl-1,3-propanediol, and having a pH of 9.5 or more and 12.5 or less at 25° C., wherein a mass ratio of (X)/(Z) is 0.1 to 1.

9. The skin cleansing composition according to claim 8, wherein the total content of the component (X) and the component (Z) is 5 mass % or more.

10. The skin cleansing composition according to claim 8, wherein the content of the component (Z) is 5 mass % or more.

11. A method for removing keratotic plugs, comprising applying to skin having keratotic plugs a composition according to claim 1.

12. The method according to claim 11, wherein said composition further comprises (A) an anionic surfactant.

13. The method according to claim 12, wherein the component (A) comprises (A1) an anionic surfactant having a carboxylic acid group and/or (A2) an anionic surfactant having a sulfonic acid group or a sulfate group.

14. The method according to claim 13, wherein a mass ratio of a content of the component (X) to a content of the component (A1), (X)/(A1), is 1 or more and 100 or less.

15. The method according to claim 13, wherein a mass ratio of a content of the component (X) to a content of the component (A2), (X)/(A2), is 0.1 or more and 100 or less.

16. The method according to claim 11, further comprising (B) a nonionic surfactant.

17. The method according to claim 16, wherein the component (B) comprises (B1) a nonionic surfactant having an HLB of 11 or more and/or (B2) a nonionic surfactant having an HLB of less than 11.

* * * * *